(12) United States Patent
Ebbrecht et al.

(10) Patent No.: US 8,268,939 B2
(45) Date of Patent: Sep. 18, 2012

(54) PROCESS FOR MODIFYING SURFACES

(75) Inventors: Thomas Ebbrecht, Wetter/Ruhr (DE); Frank Schubert, Neukirchen-Vluyn (DE); Matthias Naumann, Greensboro, NC (US); Wilfried Knott, Essen (DE); Kathrin Lehmann, Leverkusen (DE); Joachim Venzmer, Essen (DE); Berend-Jan De Gans, Muelheim an der Ruhr (DE); Stefan Silber, Krefeld (DE); Frauke Henning, Essen (DE)

(73) Assignee: Evonik Goldschmidt GmbH, Essen (DE)

( * ) Notice: Subject to any disclaimer, the term of this patent is extended or adjusted under 35 U.S.C. 154(b) by 285 days.

(21) Appl. No.: 12/630,125

(22) Filed: Dec. 3, 2009

(65) Prior Publication Data
US 2010/0184913 A1    Jul. 22, 2010

(30) Foreign Application Priority Data

Dec. 5, 2008  (DE) .......................... 10 2008 044 373
May 25, 2009  (DE) .......................... 10 2009 022 628

(51) Int. Cl.
*C08G 77/14*  (2006.01)
(52) U.S. Cl. .......................................... 525/476; 528/34
(58) Field of Classification Search .................. 525/476; 528/34
See application file for complete search history.

(56) References Cited

U.S. PATENT DOCUMENTS

| | | |
|---|---|---|
| 3,388,079 A * | 6/1968 | Vandenberg .................. 528/27 |
| 4,376,149 A | 3/1983 | Martin |
| 5,068,304 A | 11/1991 | Higuchi et al. |
| 5,401,871 A | 3/1995 | Feldmann-Krane et al. |
| 5,430,166 A | 7/1995 | Klein et al. |
| 5,475,127 A | 12/1995 | Klein et al. |
| 5,494,979 A | 2/1996 | Ebbrecht et al. |
| 5,552,506 A | 9/1996 | Ebbrecht et al. |
| 5,719,249 A | 2/1998 | Fujita et al. |
| 5,804,099 A | 9/1998 | Heilen et al. |
| 5,977,282 A | 11/1999 | Ebbrecht et al. |
| 6,054,534 A | 4/2000 | Josten et al. |
| 6,291,622 B1 | 9/2001 | Droese et al. |
| 6,307,082 B1 | 10/2001 | Klein et al. |
| 6,423,785 B1 | 7/2002 | Esselborn et al. |
| 6,552,091 B1 | 4/2003 | Boinowitz et al. |
| 6,835,420 B1 | 12/2004 | Rockrath et al. |
| 6,861,493 B2 | 3/2005 | Bauer et al. |
| 7,018,458 B2 | 3/2006 | Knott et al. |
| 7,118,619 B2 | 10/2006 | Brandt et al. |
| 7,125,585 B2 | 10/2006 | Dudzik et al. |
| 7,157,541 B2 | 1/2007 | Knott et al. |
| 7,189,772 B2 | 3/2007 | Bauer et al. |
| 7,196,153 B2 | 3/2007 | Burkhart et al. |
| 7,442,724 B2 | 10/2008 | Esselborn et al. |
| 7,598,215 B2 | 10/2009 | Hinrichs et al. |
| 7,598,334 B2 | 10/2009 | Ferenz et al. |
| 7,612,158 B2 | 11/2009 | Burkhart et al. |
| 7,612,159 B2 | 11/2009 | Burkhart et al. |
| 7,645,848 B2 | 1/2010 | Knott et al. |
| 2006/0183815 A1 | 8/2006 | Alzer et al. |
| 2007/0043193 A1 | 2/2007 | Henning et al. |
| 2007/0128143 A1 | 6/2007 | Gruening et al. |
| 2007/0213226 A1 | 9/2007 | Sieverding et al. |
| 2008/0004357 A1 | 1/2008 | Meyer et al. |
| 2008/0034794 A1 | 2/2008 | Ebbrecht et al. |
| 2008/0064782 A1 | 3/2008 | Dohler et al. |
| 2008/0125503 A1 | 5/2008 | Henning et al. |
| 2008/0153934 A1 | 6/2008 | Neumann et al. |
| 2008/0153992 A1 | 6/2008 | Knott et al. |
| 2008/0153995 A1 | 6/2008 | Knott et al. |
| 2008/0188673 A1 | 8/2008 | Lehmann et al. |
| 2008/0200576 A1 | 8/2008 | Seiler et al. |
| 2008/0275176 A1 | 11/2008 | Limin et al. |
| 2009/0007483 A1 | 1/2009 | Hansel et al. |
| 2009/0012197 A1 | 1/2009 | Landers et al. |
| 2009/0030097 A1 | 1/2009 | Knott et al. |
| 2009/0053552 A1 | 2/2009 | De Gans et al. |
| 2009/0093598 A1 | 4/2009 | Venzmer et al. |
| 2009/0137751 A1 | 5/2009 | Knott et al. |
| 2009/0137752 A1 | 5/2009 | Knott et al. |
| 2009/0149573 A1 | 6/2009 | Venzmer et al. |
| 2010/0022435 A1 | 1/2010 | Henning et al. |
| 2010/0029587 A1 | 2/2010 | Bruckner et al. |
| 2010/0036011 A1 | 2/2010 | De Gans et al. |
| 2010/0041629 A1 | 2/2010 | Knott et al. |
| 2010/0041910 A1 | 2/2010 | Schubert et al. |
| 2010/0056649 A1 | 3/2010 | Henning et al. |
| 2010/0071849 A1 | 3/2010 | Knott et al. |
| 2010/0081781 A1 | 4/2010 | Schubert et al. |
| 2010/0105843 A1 | 4/2010 | Schubert et al. |
| 2010/0113633 A1 | 5/2010 | Henning et al. |

* cited by examiner

*Primary Examiner* — Kuo-Liang Peng
(74) *Attorney, Agent, or Firm* — Frommer Lawrence & Haug LLP

(57) ABSTRACT

Use of one or more mixed curable hydroxyl-containing silyl polyethers as a constituent of compositions, as modifiers for surfaces, the silyl polyethers being prepared by DMC-catalysed alkoxylation of epoxy-functional alkoxysilanes.

11 Claims, 5 Drawing Sheets

Figure 1: Structure of the formula (1)

Formula 5a

Formula 6a

PROCESS FOR MODIFYING SURFACES

This application claims benefit under 35 U.S.C. 119(a) of German patent application DE 102008044373.5, filed on Dec. 5, 2008 and DE 102009022628.1 filed on May 25, 2009.

Any foregoing applications including German patent application DE 102008044373.5 and 102009022628.1, and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

The invention relates to a process for modifying planar and particle surfaces by means of curable compositions comprising hydroxyl compounds bearing silyl groups.

Hydroxyl compounds bearing silyl groups and used for the purposes of this invention are understood as including all reaction products which can be prepared by alkoxylation of epoxy-functional silanes over double metal cyanide catalysts in accordance with the process described in the as yet unprepublished specification DE 10 2008 000360.3; these compounds may in particular also bear siloxane groups. These products are referred to below as silyl polyethers 1. A silyl group for the purposes of this invention is characterized by identical or different organic or oxyorganic radicals represented by the structure of formula 1, see FIG. 1:

In the context of this invention, the term polyethers embraces not only polyethers, polyetherols, polyether alcohols and polyether esters but also polyether carbonates, which, where appropriate, are used synonymously with one another. In such cases it is not necessary for the expression "poly" to necessarily imply that there are a multiplicity of ether functionalities or alcohol functionalities present in the molecule or polymer. Instead this expression merely indicates that there are at least repeating units of individual monomer building blocks or else compositions which have a relatively high molar mass and also, furthermore, a certain polydispersity.

The word-fragment "poly" in connection with this invention encompasses not only exclusively compounds having at least 3 repeating units of one or more monomers in the molecule, but also, in particular, those compositions of compounds which have a molecular weight distribution and possess an weight average molecular weight ($M_W$) of at least 200 g/mol (weight average molecular weight measured by gel permeation chromatography). This definition takes account of the circumstance that, within the field of art under consideration, it is customary to designate even compounds of this kind as polymers, even when they do not appear to satisfy the definition of a polymer along the lines of OECD or REACH Guidelines.

Modification for the present purposes is the chemical or physical attachment of a modifier to the solid surface in question. Relative to the solid surface, this modification may optionally be partial or complete, the solid surface being covered with a coherent monolayer or else with a multiple layer. Modification in the sense of this definition also includes surface coatings which in general are full-area coatings, such as with paints and inks, for example.

Modifications of areas or particles in order to modify surfaces are carried out for a diversity of reasons and by a very wide variety of processes, and are known to the skilled person from the literature. The general purpose of modifications is to modify the chemical and physical properties of surfaces of a substrate material, through application of a usually thin layer of a modifier, purposively for the particular desired end-use application. For example, modifiers fulfill important functions as adhesion promoters, primers, varnishes, water repellents, or wetting agents. Common to all variants of coatings is the application of a layer with maximum adhesion to the substrate in question, through application of an often liquid or powderous, easy-to-apply modifier.

Depending on the nature of the surface to be modified, the chemophysical nature of the modifier in question, and the application-related objective of the desired surface modification, very different processes are employed for application of the layer. In addition, for example, to thermal and electrochemical processes, chemical modifying processes in particular play a prominent role.

Similarly diverse are the substrates amenable to surface modification. As well as relatively flat substrate materials such as metals, concrete, plastics, wood or glass, they include solid particles, fibres and, for example, woven textile fabrics, which are surface-modified through application of thin layers.

Hence, surfaces of inorganic particles, of macroscopic inorganic surfaces and of inorganic fibres, such as those, for example, of metal oxides, mixed oxides, nitrides, hydroxides, carbides, carbonates, silicates, pigments, carbon blacks, elements or alloys have previously been modified. Likewise, organic particles, macroscopic organic surfaces and fibres, such as those, for example, of silicone resins, organomodified silicones, organic polymers or biopolymers, can be modified.

It can be particularly advantageous if the modifier used has at least one functional group which is able to enter into covalent, ionic or coordinative bonds, or hydrogen bonds, with the surface that is to be modified. These functional groups may be, for example, carboxylic acid groups, acid chloride groups, ester groups, nitrile and isonitrile groups, OH groups, SH groups, epoxide groups, anhydride groups, acid amide groups, primary, secondary and tertiary amino groups, SiOH groups, hydrolysable alkoxysilanes or CH-acidic moieties such as those, for example, in β-dicarbonyl compounds, examples being acetylacetone, 2,4-hexanedione, 3,5-heptanedione, diacetyl or acetoacetic acid.

It is also possible for there to be more than one such group in the modifier, such as, for example, in betaines, amino acids, examples being glycine, alanine, β-alanine, valine, leucine, isoleucine, arginine and aminocaproic acid, and also in EDTA. Carboxylic acids for surface modification are, for example, fatty acids, formic acid, acetic acid, propionoic acid, butyric acid, pentanoic acids, hexanoic acid, (meth) acrylic acid, adipic acid, succinic acid, fumaric acid, itaconic acid, stearic acid, hydroxystearic acid, ricinolic acid and polyether carboxylic acids and their corresponding stereoisomers, anhydrides, chlorides, esters and/or amides, examples being methoxy acetic acid, 3,6-dioxaheptanoic acid and 3,6, 9-trioxadecanoic acid and also the corresponding acid chlorides, acid esters and acid amides, or else modifiers which carry cationic groups.

It is of particular advantage if at the same time, on the surface of the substrate to be modified, there are also functional groups such as hydroxyl groups, SH groups, amino groups or, for example, carboxylic acid groups, so that intense physical interactions are able to form between substrate material and modifier, or there are chemical reactions between reactive functional groups of the modifier and those on the substrate surface. In this way the modifier is durably anchored on the substrate in question. The chemical attachment of the modifier to the substrate material, in particular, is an efficient method, and one which is widespread in practice, for preventing subsequent detachment of the coating, under the influence of water or solvents, for example, and of ensuring a permanent surface quality which does not alter even over a prolonged time period.

The nature of the physically or chemically active anchor group in the modifier must in every case be tailored precisely to the nature and type of the reactive functional groups on the substrate surface. Important further selection criteria for selecting the best-suitable modifier are the pH, moisture content or the porosity of the respective substrate.

Consequently there is no one chemical system for surface modification that can be used universally for all types of surfaces, but rather there are a multiplicity of classes of compound, usually carrying reactive groups, which are employed for surface modification. The prior art lists, for example, reactive monomeric and polymeric compounds containing isocyanate, epoxide, acrylate, silane, carboxylate, amine, hydroxyl and mercapto functions, these compounds being fixed on the substrate by a variety of chemical/physical routes depending on the substrate.

In addition to the functional group capable of attachment to the substrate, the modifier may have other radicals which help modify the surface properties of the substrate. Such radicals, or else parts thereof, may be, for example, hydrophobic or hydrophilic, or may carry one or more functional groups in order thus to make particulate solids or else fibres compatible with the surrounding medium, to render them inert or to render them reactive with respect, for example, to further materials to be attached, also including attachment to the surrounding matrix. These functional groups may be selected, for example, from the range of alkyl, aryl, alkaryl, aralkyl, fluoroalkyl, hydroxyl, alkoxy, polyalkoxy, epoxy, acryloyloxy, methacryloyloxy, acrylate, methacrylate, carboxyl, amino, sulphonyl, sulphate, phosphate, polyphosphate, phosphonate, amide, sulphide, hydrogen sulphide, haloalkyl, haloaryl, acyl and ionic, anionic for example, cationic or amphoteric groups.

The most widespread modifiers include silanes which can be crosslinked by hydrolysis of the formula (2),

$$A_xSiB_{(4-x)} \quad (2)$$

where A represents identical or different non-hydrolysable groups, B=identical or different hydrolysable groups or hydroxyl groups, and x=1, 2, 3 or 4.

In the general formula (2) the hydrolysable groups B may be, for example, H, halogen, alkoxy, preferably methoxy, ethoxy, isopropoxy, n-propoxy or butoxy, aryloxy, preferably phenoxy, acyloxy, preferably acetoxy or propionyloxy, acyl, preferably acetyl, amino, monoalkylamino or dialkylamino groups. The non-hydrolysable radical A may be, for example, an alkyl, alkenyl, alkynyl, aryl, alkylaryl or aralkyl radical. The alkyl chain may have 0 to 50, preferably 0 to 22, carbon atoms and may also be interrupted by heteroatoms such as oxygen or nitrogen or sulphur, or else may be a silicone radical. The aromatic radical may also be heteroaromatic. The radicals A and B may where appropriate contain one or more customary substituents, such as halogen or alkoxy, for example.

Non-hydrolysable radicals A according to the formula (2) with functional groups may be selected from the range of the glycidyl or glycidyloxyalkylene radicals, such as, for example, β-glycidyloxyethyl, γ-glycidyloxypropyl, δ-glycidyloxypropyl, ε-glycidyloxypentyl, ω-glycidyloxyhexyl or 2-(3,4-epoxycyclohexyl)ethyl, the methacryloyloxyalkylene and acryloyloxyalkylene radicals, such as, for example, methacryloyloxymethyl, acryloyloxymethyl, methacryloyloxyethyl, acryloyloxyethyl, methacryloyloxypropyl, acryloyloxypropyl, methacryloyloxybutyl or acryloyloxybutyl, and the 3-isocyanatopropyl radical, and/or cyclic and/or linear, (poly)urethane group-containing and/or urea-containing and/or (poly)amine-group-containing radical.

Particularly widespread is the use of low-viscosity monomeric compounds which carry trimethoxysilyl and triethoxysilyl groups and which, in the presence of atmospheric moisture and suitable catalysts, are able, usually just at room temperature, to undergo condensation with one another, with elimination of the alkoxy groups and formation of Si—O—Si bonds. Organofunctional monomeric silanes of this kind are, for example, N-cyclohexylaminomethyltrimethoxysilane, N-cyclohexyl-3-aminopropyltriethoxysilane, 3-aminopropyltrimethoxysilane, vinyltrimethoxysilane, vinyltriethoxysilane, vinyldimethoxymethylsilane, 3-isocyanatopropyltrimethoxysilane, 3-glycidyloxypropyltrimethoxysilane, 3-glycidyloxypropyltriethoxysilane, 3-methacryloyloxypropyltrimethoxysilane, methyltrimethoxysilane, methyltriethoxysilane, dimethyldimethoxysilane, phenyltriethoxysilane and hexadecyltrimethoxysilane. An entry point into this topic is offered by "Silylated Surfaces", edited by Donald E. Leyden and Ward T. Collins, Gordon and Breach Science Publishers, Inc., 1980, ISBN 0-677-13370-7.

Besides monomeric organosilanes, prepolymer systems and sol-gel materials are known (on this point see also "Sol-Gel-Science: The Physics and Chemistry of Sol-Gel Processing", C. Jeffrey Brinker, George W. Scherer, Academic Press Inc., 1990, ISBN 0-12-134970-5), as are mixtures thereof which possess reactive alkoxysilyl groups and are widely used for producing coatings and also elastic sealants and adhesives in the industrial and construction sectors. For instance, alkoxysilane-functional polyurethanes which crosslink via a silane polycondensation have been known for a long time. A review article on this topic is found, for example, in "Adhesives Age" April 1995, page 30 ff. (authors: Ta-Min Feng, B. A. Waldmann). Alkoxysilane-terminated, moisture-curing, one-component polyurethanes of this kind are being used increasingly as flexible coating, sealing and adhesive compositions in construction and in the automotive industry.

Alkoxysilane-functional polyurethanes of this kind can be prepared in accordance with U.S. Pat. Nos. 3,627,722 or 3,632,557, by, for example, reacting polyether polyols with an excess of polyisocyanate to give an NOC-containing prepolymer, which is then further reacted in turn with an aminofunctional alkoxysilane. The alkoxysilane-functional prepolymer formed contains urea and urethane groups in a high concentration, leading to high viscosity on the part of the products. WO 2007/025667 (US 2007-0055010) describes polyurethane prepolymers which additionally contain modified alkoxysilane groups and which are said to have a reduced viscosity.

One particularly widespread type of alkoxysilane-functional prepolymers are alkoxysilane-terminated prepolymers. These prepolymers may be constructed from different building blocks. Typically these prepolymers possess an organic backbone, i.e. they are composed, for example, of polyurethanes, polyethers, polyesters, polyacrylates, polyvinyl esters, ethylene-olefin copolymers, styrene-butadiene copolymers or polyolefins, and described in references including EP 0 372 561 (U.S. Pat. No. 5,068,304), WO 00/37533 (U.S. Pat. No. 6,401,925) or U.S. Pat. No. 6,207,766. Also widespread, in addition, are systems, however, whose backbone is composed wholly or at least in part of organosiloxanes, described in references including WO 96/34030 (U.S. Pat. No. 6,441,118).

One preparation process known from the prior art for alkoxysilane-terminated prepolymers starts from polyols, from polyether polyols or polyester polyols, for example, which in a first reaction step are reacted with an excess of a diisocyanate or polyisocyanate. Subsequently the resultant isocyanate-terminated prepolymers are reacted with aminoalkyl-functional alkoxysilanes to give the desired alkoxysilane-terminated prepolymer. Alternatively, alkoxysilane-terminated prepolymers can also be prepared by reacting a polyol or an OH-functional polyurethane, of the kind preparable through the reaction of polyols with a substoichiometric amount of diisocyanates or polyisocyanates, with an isocyanatoalkyl-functional alkoxysilane. These preparation processes are described in EP 1 421 129 (U.S. Pat. No. 7,153,923) or WO 2005/000931 (US 2007-0100111), for example. There are also other preparation processes that may be presented, an example being the reaction as described in WO 02/034838 (U.S. Pat. No. 7,051,001) of amino-functional polyols with carbamatoalkyl-alkoxysilanes.

Also known, furthermore, are alkoxysilane-functional prepolymers having a poly(meth)acrylate backbone. These prepolymers are typically synthesized by a copolymerization of (meth) acryloyloxyalkylalkoxysilanes with other (meth) acrylic monomers and/or with other unsaturated monomer building blocks, such as styrene. Furthermore it is also possible for alkoxysilane-functional polymers to be prepared by subsequent graft attachment of unsaturated alkoxysilanes, such as of vinylsilanes or (meth)acrylsilanes, for example.

A disadvantage of the prepolymers described is the low functionalization density of the prepolymers terminated only singularly or at most terminally in α,ω position with silyl groups. The silyl modification is often inadequate to address effectively the desired effect of good and permanent substrate adhesion. Accordingly the teaching of WO 2008/058955 relates to the option of adding free monomeric silanes as a second component to the prepolymers terminated only in α,ω position with silyl groups, in order to produce the desired effects discussed at the outset (promotion of adhesion, drying, crosslinking and so on). This in no way ensures the purposive incorporation of silyl anchor groups at the locations in the polymer that require their positive effect.

The object, therefore, was to overcome the disadvantages of the prior-art compounds and to provide improved coating materials that in terms of their chemical structure are tailored flexibly and optimally to the particular substrates and processing conditions.

Surprisingly it has now been found that the technical restrictions and disadvantages set out here can be overcome by carrying out the surface modification and coating of particles and other planar substrates using compositions comprising as a component one or more mixed curable hydroxyl-containing silyl polyethers having at least one non-terminal silyl function, preferably more than one non-terminal silyl function, and more preferably more than one non-terminal silyl function and also, at the same time, at least one terminal silyl function in the molecule. In particular they contain more than one (1) alkoxysilyl function per chain end reactive towards epoxide groups. These compounds are obtainable by alkoxylating epoxide-functional alkoxysilanes over double metal cyanide (DMC) catalysts, and are described in the as yet unpublished specification DE 10 2008 000360.3, which is hereby introduced in full as part and subject matter of the present disclosure.

These new hydroxyl compounds, bearing silyl groups, of the formula 1, which may contain not only alkoxysilane functions within the sequence of the oxyalkylene units of the polyether chain but also new alkoxysilane functions in their termini, allow the setting of the density of anchor groups in the target prepolymer arbitrarily, in other words adapted to the particular application-related objective. These polyether structures may also be attached via an SiC or SiOC bond to linear or branched polysiloxane structures.

These innovative reactive polyethers and/or polyethersiloxanes, on account of their alkoxysilyl groups, which are sensitive to hydrolysis and exhibit a propensity towards crosslinking, represent curable polymers. Their crosslinking to solid thermoset end products, or their chemical attachment to reactive surfaces, such as to particle surfaces, for example, is readily accomplished optionally with addition of water, acid or base as accelerant, the curing time being controllable through an increase in temperature during the curing operation. Accordingly the polymer architecture of these crosslinkable polyethers and polyethersiloxanes can be multivariously varied in accordance with the nature of the initiator and siloxane structure and with the nature, amount and sequence of the epoxide monomers that can be used, in order thus to custom-tailor important performance product properties as a function of the particular end use. Thus, for example, by varying the fraction of alkoxysilane units in the polymer chain, it is possible to influence the crosslinking density and hence the mechanical and physiochemical properties profile of the cured systems, within wide limits.

Surprisingly here, even polyethers and polyethersiloxanes furnished with a considerable alkoxysilyl functionalization density are, at room temperature and atmospheric pressure, liquids of low viscosity which can be handled readily and have viscosities of typically below 1000 mPas, and, consequently, there are no restrictions on the metering of this component.

This observation differentiates the inventive teaching from the procedure set out in WO 2008/058955, which is geared to the incorporation of free silane monomers as, formulating ingredients into the end formulas in order to ensure that the necessary crosslinking density is obtained in conjunction with a low processing viscosity. The polyethers containing alkoxysilyl groups, with virtually no limitations to their structural diversity, and the corresponding siloxane copolymers, provide a person skilled in the polymer chemistry art with a freedom of design through the incorporation, for example, of ester, carbonate and aromatic structural elements into the polyether structure, this freedom being such as to address virtually any performance requirements. Even greater is the diversity of possible alkoxysilyl polyether-siloxane copolymer structures, since each organic radical is attached singularly or multiply, terminally or, to a polysiloxane backbone which is linear or branched to different degrees, is variable in its molar mass and is additionally modified, if required, by other carbon radicals, the chemical linking of the organic polyether component taking place optionally via an SiC or an SiOC bond. Use may also be made of any desired mixtures of alkoxysilyl polyethers with silicone polyethers bearing alkoxysilyl groups.

In contrast, conventional organic polymers, as described in WO 2005/100482, for example, contain no silyl groups within their main chain or the main chains, but instead contain silyl groups only on the respective ends of the polymer chains. Thus in a linear polymer only the two ends of the polymer are silyl-terminated; a polymer of this kind is referred to below as divalent. In the case of the use of a polymer prepared starting, for example, from glycerol, it is possible, starting from the three hydroxyl groups of the glycerol, for three independent silyl-free polymer strands to form, and, in turn, a silyl group terminus can be attached only to the end of the strand. A three-ended polymer branched in this way is referred to below as trivalent. By analogy, polymers with four ends are referred to as tetravalent.

The absence of further silyl groups in the structures of DE 10 2004 018548 within the base polymer chain, in the form of side groups, for example, limits the crosslinking density and also the adhesion after curing. In the case of crosslinking via side groups, the adhesion may be increased by means of additional anchor groups on the substrate in question, or else adapted through the appropriate choice of silyl functionalization, dependent on the application. By means of measures including, among others, appropriate structural selection, the time window of curing is therefore placed at the whim of the user; at the same time it is also possible in this way to carry out purposeful preparation of particle-comprising compositions possessing outstanding stability on storage.

The invention accordingly provides for the use of curable silyl polyethers 1 as a constituent of compositions which can be used as modifiers for surfaces, prepared by DMC catalysed alkoxylation of epoxy-functional alkoxysilanes. The surfaces may be formed microscopically, in the form for example of particles or particle agglomerates, and/or macroscopically, in the form of planar structures or fibres or similar three-dimensional bodies.

For particle modification it is preferred to use silyl polyethers 1 of the formula (1)—see also FIG. 1. These polyethers are composed of alkoxysilyl-substituted chains which, through the choice of the fragments d to j, corresponding to the fragments inserted into the polymer chain by the reaction, with ring opening, of the reaction components, have a specifically high degree of functionalization and hence can be tailored to many different kinds of fields of application.

Silyl polyether 1 of the formula (1) (see FIG. 1)

where a is an integer from 1 to 3, preferably 3, b is an integer from 0 to 2, preferably 0 to 1, more preferably 0, and the sum of a and b is 3, c is an integer from 0 to 22, preferably from 0 to 6, more preferably 1 or 3, d is an integer from greater than 1 to 1000, preferably greater than 1 to 100, more preferably greater than 1 to 20, and more particularly greater than 1 to 10, or greater than 10 to 100, e is an integer from 0 to 10 000, preferably 0 to 1000, more preferably 0 to 300, and more particularly 0 to 100, f is an integer from 0 to 1000, preferably 0 to 100, more preferably 0 to 50, and more particularly 0 to 30, g is an integer from 0 to 1000, preferably 0 to 200, more preferably 0 to 100, and more particularly 0 to 70, h, i and j are integers from 0 to 500, preferably 0 to 300, more preferably 0 to 200, and more particularly 0 to 100, and with the proviso that the fragments having the indices d to j are freely permutable with one another, i.e. are interchangeable in the sequence within the polyether chain, n is an integer between 2 and 8, and R represents one or more identical or different radicals selected from linear or branched, saturated, singularly or multiply unsaturated alkyl radicals having 1 to 20, more particularly 1 to 6, carbon atoms or haloalkyl groups having 1 to 20 carbon atoms. Preferably R corresponds to methyl, ethyl, propyl, isopropyl, n-butyl and sec-butyl groups, and especially ethyl or methyl groups, and $R^1$ is a saturated or unsaturated, optionally branched radical which is preferably attached via an oxygen atom, or is a polyether radical of the type of an alkoxy, arylalkoxy or alkylarylalkoxy group, in which the carbon chain may be interrupted by oxygen atoms, or $R^1$ is an optionally singularly or multiply fused aromatic aryloxy group, or is a silicon compound, in particular a siloxane radical, which may be substituted by alkyl and/or aryl groups and/or polyether, $R^2$ or $R^3$, and $R^5$ or $R^6$, is or else are independently of one another H or a saturated or optionally singularly or multiply unsaturated, including further substituted, optionally monovalent or polyvalent hydrocarbon radical, the radicals $R^5$ or $R^6$ being a monovalent hydrocarbon radical. The hydrocarbon radical may be bridged cycloaliphatically via the fragment Y; Y may be absent, or else may be a methylene bridge having 1 or 2 methylene units; if Y is absent, then $R^2$ or $R^3$ independently of one another are each a linear or branched radical having 1 to 20, preferably 1 to 10, carbon atoms, more preferably a methyl, ethyl, propyl or butyl, vinyl, allyl or phenyl radical. Preferably at least one of the two radicals, $R^2$ or $R^3$, is hydrogen. $R^2$-$R^3$ may be a —$CH_2CH_2CH_2CH_2$— group, and Y may therefore be a —($CH_2CH_2$—)— group. The hydrocarbon radicals $R^2$ and $R^3$ may in turn be further substituted and may carry functional groups such as halogens, hydroxyl groups or glycidyloxypropyl groups.

$R^4$ is a linear or branched alkyl radical of 1 to 24 carbon atoms or an aromatic or cycloaliphatic radical, which optionally may in turn carry alkyl groups, $R^7$ and $R^8$ are independently of one another either hydrogen, or alkyl, alkoxy, aryl or aralkyl groups which are copolymerized by ring-opening polymerization to give crosslinkable polyether esters containing alkoxysilane groups.

$R^9$, $R^{10}$, $R^{11}$ and $R^{12}$ are independently of one another either hydrogen or alkyl, alkenyl, alkoxy, aryl or aralkyl groups. The hydrocarbon radical may be bridged cycloaliphatically or aromatically via the fragment Z, it being possible for Z to be a divalent alkylene or alkenylene radical.

It can be advantageous if the silyl polyethers of the formula (1) are those containing exclusively radicals $R^1$ which contain silicon atoms, or those containing exclusively radicals $R^1$ which have no silicon atoms.

The various monomer units both of the fragments having the index numbers d to j and also of the polyoxyalkylene chain of the substituent $R^1$, where present, may individually be of blockwise structure or else may be subject to a random distribution. The index numbers reproduced in the formulae given here, and the ranges of values for the indices given, are therefore understood to be the average values of the possible random distribution of the structures and/or mixtures thereof that are actually present. This also applies to structural formulae which as such are reproduced exactly per se, such as for formula (1), for example.

Very particularly preferred monomers are 3-glycidyloxyalkyltrialkoxysilanes and 3-glycidyloxyalkyldialkoxyalkylsilanes.

As is evident from $^{29}$Si NMR and GPC analyses, the process-related presence of chain-terminal OH groups brings about the possibility for transesterification reactions on the silicon atom not only during the DMC-catalysed preparation but also, for example, in a downstream process step. In such reactions, formally, the alkyl radical R attached to the silicon via an oxygen atom is replaced by a long-chain modified alkoxysilyl polymer radical. Bimodal and multimodal GPC curves are evidence that the alkoxylation products contain not only the untransesterified species, as reproduced in formula (1), but also those with twice, in some cases three times or even four times, the molar mass. Formula (1) is therefore only a simplified representation of the complex chemical reality.

Consequently the compositions also comprise compounds in which the sum of the indices (a) plus (b) in formula (1) is on average less than 3, since some of the OR groups may be replaced by silyl polyether groups. The compositions therefore include species which are formed on the silicon atom with elimination of R—OH and condensation reaction with the reactive OH group of a further molecule of the formula (1). This reaction may proceed a number of times until, for example, all of the RO groups on the silicon have been replaced by further molecules of the formula (1). The presence of more than one signal in typical $^{29}$Si NMR spectra of these compounds underscores the incidence of silyl groups having different substitution patterns. The stated values and ranges of preference for the indices a to j are therefore also to be understood only as average values over the various species, which cannot be pinned down individually.

Depending on the epoxide-functional alkoxysilane used and any further monomers employed, and also, optionally, carbon dioxide, it is possible to prepare silyl polyethers 1 of different structure, and also their arbitrarily constructed mixtures. The alkoxysilane unit in the compound of the formula (1) is preferably a trialkoxysilyl unit.

The silyl polyethers 1 of the formula (1) can be used alone or in any desired combination, blended with monomeric alkoxysilanes, alkoxysilyl-terminated prepolymers, curing catalysts and also further adjuvants and auxiliaries, in the mixture with the macroscopic surfaces and/or solid particles to be coated.

The present invention accordingly also, further, provides compositions which in addition to the silyl polyethers 1 (1) also comprise other silyl compounds, especially those of the formula (2). The silyl polyethers 1 of the formula (1) that are used with preference are those with d>1. By virtue of their numerous reactive anchor groups, they allow improved adhesion to the macroscopic surface or else particle surface in question, relative to that possible in the prior art using customary monomeric silanes such as those of formula (2), or using α,ω-silyl-terminated prepolymers.

By adaptation of the structural architecture of the polymer framework, in other words, for example, through introduction of ester groups or carbonate groups or aromatic structural elements, by setting of a desired molar mass, optionally blockwise or statistical monomer sequence, through to the alkoxysilyl functionality, the profile of properties can be adapted flexibly to the particular requirements of the overall system, in order, for example, to ensure ideal adhesion to the particle surface, to set the processing properties (e.g. viscosity) during particle modification, or to promote compatibilization of the particles in the respective matrix.

It is preferred to use curable silyl polyethers 1 having more than 1 alkylsilyl function, very preferably those having on average more than one such silyl group per terminal hydroxyl group in compositions which can be used for surface modification.

The silyl polyethers 1 provide the synthetic freedom to choose between polyoxyalkylene compounds containing alkoxysilyl groups which comprise the alkoxysilyl functions—crosslinkable through hydrolysis—either terminally or in isolation, in blocklike accumulation, or else inserted randomly into the polyoxyalkylene chain. A feature of silyl polyethers 1 of the formula (1) of this kind is that, in terms of structural architecture and molar mass, they can be prepared purposively and reproducibly. The sequence of the monomer units can be varied within wide limits. Epoxide monomers can be incorporated, as desired, either in blockwise sequence or randomly into the polymer chain. The fragments inserted, by the reaction with ring opening of the reaction components, into the polymer chain which forms are freely permutable with one another in their sequence, with the restriction that cyclic anhydrides and also carbon dioxide are present in random insertion, in other words not in homologous blocks, in the polyether structure.

As the skilled person is aware, the crosslinking or curing of alkoxysilyl groups takes place in a two-stage chemical process in which, in a first step, in the presence of water—for which atmospheric moisture may also be sufficient—the alkoxy groups attached to the silicon are eliminated in the form of the corresponding alcohols, and SiOH groups are formed. In the case of self-condensation, the latter groups condense subsequently with one another, with formation of Si—O—Si bridges, and polymeric materials are formed. The SiOH-functional intermediates preferably react with substrates containing reactive groups, as, for example, particularly well with silicatic surfaces which bear OH functions, and lead to excellent chemical anchoring on the substrate in question. The cure rate can be influenced in a diversity of ways through addition of catalysts or through temperature variation.

Where the polyethers used as silyl polyethers 1 are those containing more than 1 of the highly functionalized polyalkylene ether fragments attached to the silicon atom, then highly functionalized compounds are present in which polyether chains each derived from a starting alcohol of the formula (3) $R^1$—H (the H belongs to the OH group of the OH-containing compound used as starter, here referred to as starting alcohol) and containing in their sequence the freely permutable fragments which were inserted by the reaction, with ring opening, of the reaction components into the resultant polymer chain, are linked to one another via —CH$_2$—O—(CH$_2$)$_c$—Si—(CH$_2$)$_c$—O—CH$_2$— bridges. These are highly complex, highly functionalized structures. As well, the functionalities can be set purposively for a desired field of use. The degree of branching and the complexity of the polymer structures obtained increase in line with the epoxy functionality of the silyl monomers. The chain length of the polyether radicals which can be used as starting compound and contain alkoxy, arylalkoxy or alkylarylalkoxy groups is arbitrary. The polyether, alkoxy, arylalkoxy or alkylarylalkoxy group contains preferably 1 to 1500 carbon atoms, more preferably 2 to 300 carbon atoms, and especially 2 to 100 carbon atoms. OH-functional starting compounds used, $R^1$—H (3), are preferably compounds having molar masses of 18 to 10 000 g/mol, more particularly 50 to 2000 g/mol, and having 1 to 8, preferably 1 to 4, hydroxyl groups. If, however, a siloxane moiety is to be introduced as $R^1$ into the silyl polyether, then use is made, for example, of α,ω-dihydroxypolysiloxanes, hydrogensiloxanes or hydroxyl-functional polyethersiloxanes as starting compounds. The siloxane elements of these radicals $R^1$ correspond to the structures described in formula (5) or (6).

Especially suitable modifiers for surfaces and/or coatings are the polyethersiloxanes bearing alkoxysilane units. The content of the description and the claims is hereby considered in full to be part of the present disclosure content.

If, therefore, a (poly-)siloxane radical is introduced as $R^1$ into the molecule, then alkoxysilyl-functional polyethersiloxanes are used in accordance with the invention.

These alkoxysilyl-functional polyethersiloxanes and mixtures thereof can be prepared by two different processes:
1) alkoxylation of silicone polyether copolymers and polysiloxanes with epoxy-functional alkoxysilanes over double metal cyanide catalysts
   and/or
2) hydrosilylating linkage of unsaturated alkoxysilyl-bearing polyethers obtained beforehand by alkoxylating the corresponding unsaturated starting compounds with epoxy-functional alkoxysilanes over DMC catalysts.

The alkoxysilyl-functional polyethersiloxanes are compounds of formula (5) and mixtures thereof,

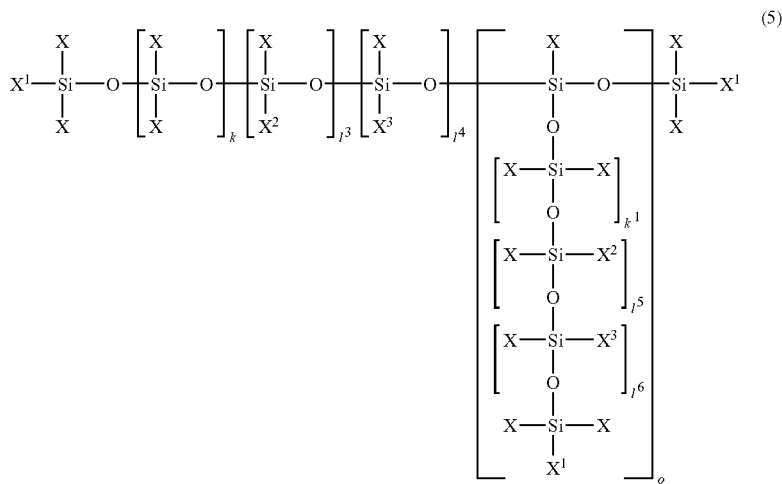

(5)

where
X is a linear, cyclic or branched, aliphatic or aromatic, saturated or unsaturated hydrocarbon radical having 1 to 20 C atoms, which can if desired contain heteroatoms such as oxygen, nitrogen, phosphorus or sulphur, but is preferably a methyl group,
$X^1$ is independently X, $X^2$ or $X^3$,
$X^2$ is an alkoxysilyl-bearing, OH-functional polyoxyalkylene radical of the formula (5a) which is optionally ester- or carbonate-modified—see also FIG. 2,
(5a)—see FIG. 2
$X^3$ is a terminally etherified polyoxyalkylene radical of the formula (5b),

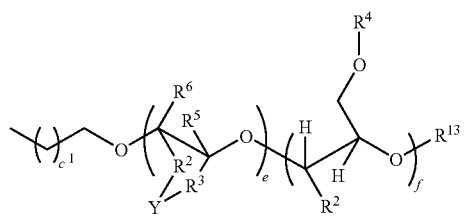

(5b)

where
$R^{13}$ is optionally an alkyl group having 1 to 18 C atoms, preferably methyl, or a polyoxyalkylene radical which is terminally esterified with a monofunctional carboxylic acid, of the formula (5c),

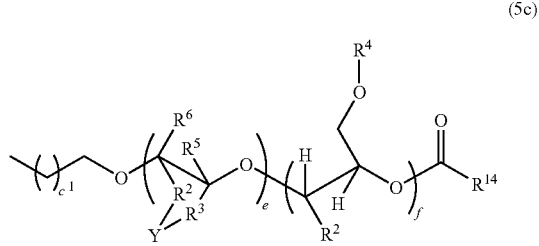

(5c)

where
$R^{14}$ is a saturated or a singularly or multiply unsaturated, either linear or branched, aliphatic or aromatic hydrocarbon radical having 1-30 carbon atoms, which in its turn may carry OH groups, preferably a methyl radical,
$X^4$ is either $X^1$ or the fragment of the formula (5d)

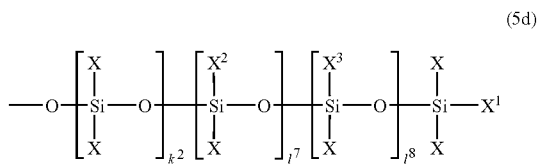

(5d)

where
k, $k^1$ and $k^2$ independently of one another are integers from 0 to 500, preferably from 10 to 200, more particularly 15 to 100,
$l^3, l^4, l^5, l^6, l^7$ and $l^8$ independently of one another are integers from 0 to 60, preferably from 0 to 30, more particularly from 0 to 25,
o is an integer from 0 to 10, preferably from 0 to 3, with the proviso that
$X^1$ is at least once $X^2$, if the sum of $l^3, l^5$ and $l^7$ is zero,
and that the sum of $l^3, l^5$ and $l^7$ is at least 1 if $X^1$ is other than $X^2$,
where
a is an integer from 1 to 3, preferably 3,
b is an integer from 0 to 2, preferably 0 to 1, more preferably 0,
the sum of a and b is 3,
c is an integer from 0 to 22, preferably from 0 to 6, more preferably 1 or 3,
$c^1$ is an integer from 0 to 24, preferable from 0 to 12, more preferably from 0 to 8, very preferably from 0 to 4, more particularly 1, d is an integer from greater than 1 to 1000, preferably greater than 1 to 100, more preferably greater than 1 to 20, and more particularly greater than 1 to 10, or greater than 10 to 100, e is an integer from 0 to 10 000, preferably 0 to 1000, more preferably 0 to 300, and more particularly 0 to 100, n is an integer from 2 to 8, and f, g, h, i and j are each integers from 0 to 500, preferably 0 to 300, more preferably 0 to 200, more particularly 0 to 100, with the proviso that the fragments having indices d to j are freely permutable with one another, i.e. interchangeable in the sequence within the polyether chain, it being possible for the various monomer units of the fragments having the index numbers d to j to be of blockwise structure with one another or else to be subject to a statistical distribution and with the proviso that the fragments having the indices k, $k^1$, $k^2$, $l^3$, $l^4$, $l^5$, $l^6$, $l^7$, $l^8$, and o are freely permutable with one another, i.e. interchangeable within the siloxane chain, and may optionally be present in random distribution or in blocklike array.

R represents one or more identical or different radicals selected from linear or branched, saturated, singularly or multiply unsaturated alkyl radicals having 1 to 20, more particularly 1 to 6, carbon atoms or haloalkyl groups having 1 to 20 carbon atoms, preferably a methyl, ethyl, propyl, isopropyl, n-butyl or sec-butyl group.

$R^2$ or $R^3$, and $R^5$ or $R^6$, are each or independently of one another H or a saturated or optionally singularly or multiply unsaturated, including further substituted, optionally monovalent or polyvalent hydrocarbon radical, the radicals $R^5$ or $R^6$ being a monovalent hydrocarbon radical. The hydrocarbon radical may be bridged cycloaliphatically via the fragment Y; Y may be absent, or else may be a methylene bridge having 1 or 2 methylene units; if Y is 0, then $R^2$ or $R^3$ independently of one another are each a linear or branched radical having 1 to 20, preferably 1 to 10, carbon atoms, more preferably a methyl, ethyl, propyl or butyl, vinyl, allyl radical or phenyl radical. Preferably at least one of the two radicals in $R^2$ or $R^3$ is hydrogen. The hydrocarbon radicals $R^2$ or $R^3$ may in turn be further substituted and carry functional groups such as halogens, hydroxyl groups or glycidyloxypropyl groups.

$R^4$ is a linear or branched alkyl radical of 1 to 18 carbon atoms, which may be attached to an aromatic or cycloaliphatic radical.

$R^7$ and $R^8$ are independently of one another either hydrogen or alkyl, alkoxy, aryl or aralkyl groups.

$R^9$, $R^{10}$, $R^{11}$ and $R^{12}$ are independently of one another either hydrogen or alkyl, alkenyl, alkoxy, aryl or aralkyl groups, the hydrocarbon radical being bridged cycloaliphatically or aromatically via the fragment Z, it being possible for Z to be a divalent alkylene or else alkenylene radical.

The polyethersiloxanes described by formula (5) include the by-products that may be present as a result of the process, such as free, excess polyethers or rearrangement products, as well.

The different monomer units within the siloxane chain and/or within the polyether chain linked to it may each optionally be blockwise or randomly arranged. The index numbers reproduced in the formulae given here, and the value ranges for the indices indicated, are to be understood as the average values of the possible statistical distribution of the actual isolated structures and/or mixtures thereof. This applies even in the case of structural formulae which as such are reproduced exactly per se.

Very particular preference is given to 3-glycidyloxyalkyl-trialkoxysilane and 3-glycidyloxyalkyldialkoxyalkylsilane monomers.

The polyethersiloxanes with alkoxysilyl functionalization, of the formula (5), usually represent copolymers with comb-like branching, in which the polyether chains are each attached via SiC bonds to the polysiloxane backbone.

Likewise possible for use in accordance with the invention are linear polyether-siloxane-polyether triblock copolymers of the formula (6) in which the polyether chains furnished with alkoxysilyl groups are attached via an Si—O—C linkage, obtained for example from dehydrogenative coupling reactions, to the siloxane structure,

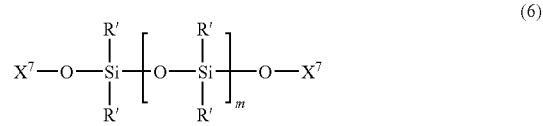

(6)

where

R' corresponds to one or more identical or different linear or branched, saturated, singularly or multiply unsaturated alkyl radicals having 1 to 20, more particularly 1 to 10, carbon atoms, and m is an integer from 0 to 5000, preferably 2 to 5000, more preferably from 5 to 4000, and more particularly 9 to 3000, and $X^7$ corresponds to the polyether fragment of the formula (6a)—see FIG. 3.

The substituents R, $R^2$-$R^{12}$, the radicals Y and Z, and the indices a, b, c, d, e, f, g, h, i, j and n correspond to the definitions specified above for the compounds of the formula (5a).

The index numbers reproduced in the formulae (5) to (5d) and (6) and also (6a), and the value ranges for the indices indicated, are to be understood as the average values of the possible statistical distribution of the actual structures present and/or mixtures thereof.

The alkoxysilane polymers of the formulae (1), and the siloxane-group-containing structures of the formulae (5) and (6), can be used alone or in any desired combination, blended with monomeric alkoxysilanes, alkoxysilyl-terminated prepolymers, alkoxysilyl-modified siloxanes, of the kind obtainable, for example, by hydrosilylation of hydrogen siloxanes with vinyl-substituted alkoxysilanes, silicone resins, curing catalysts, and also further additives and auxiliaries, which add together to make 100 parts in total.

The abovementioned silane polymers of formula (1) which can be used in accordance with the invention may also be employed as components in mixtures with conventional monomeric silanes of the formula (2),

(2)

where A represents identical or different non-hydrolysable groups, B=identical or different hydrolysable groups or hydroxyl groups, and x=1, 2, 3 or 4. By virtue of their low viscosity, the silyl polyethers 1 can also be used in combination with other, conventional silyl-terminated polymers, of higher viscosity, for example, whose viscosity is usually greater than 10 000 mPas, in order to lower the viscosity of the system as a whole and to enhance the processing properties. Highly alkoxysilyl-functional prepolymers of the formula (1) increase the network density, ensure the requisite good chemical attachment to the substrates, and lead ultimately to high-strength coatings or surface modifications.

In addition to the alkoxysilyl-containing compounds (1) which can be used in accordance with the invention, the modifiers may also be admixed with further organomodified additives capable of hydrolytic reactive crosslinking, more particularly with those which carry organoalkoxysiloxane units and are not necessarily described by formulae above.

In this context, the fragments introduced into the resultant polymer chain through the reaction with ring opening may be distributed blockwise or randomly in the context of the preceding definitions and may occur not only in the chain of a polyether structural unit but also randomly distributed over the multiplicity of polyether structural units that are formed and that are joined to one another via —$CH_2$—O—$(CH_2)_c$—Si—$(CH_2)_c$—O—$CH_2$-bridges. The multivarious nature of the structural variations of the process products does not, therefore, allow description in the form of an unambiguous formula.

Surfaces of solid or else porous particles may be coated in accordance with the invention using methods that are known from the prior art. These methods include the spraying of the silyl polyethers 1 onto the particles with mixing, where appropriate with mixing, kneading and/or heating optionally in the presence of suitable crosslinking catalysts. The silyl polyethers of the invention, as they are or from suitable organic and/or inorganic solvents, may also be applied to the particle surfaces, where they are then able to react fully, with covalent attachment. Another possibility is to apply emulsions of the silyl polyethers 1 of the invention in suitable media, where appropriate with addition of auxiliaries, other modifiers, and emulsifiers and/or wetting agents, to the particle surfaces. The modification of particle surfaces in a matrix of (pre-)dispersed particles as well, such as, for example, of particulate filler or functional particles (pre-)dispersed in a polymer or a coating material, is possible through addition of the silyl polyethers to the corresponding systems with thorough mixing, where appropriate with heating and/or with the addition of a suitable catalyst. In each case the silyl polyethers 1 may also be admixed with further components, such as, for example, monomeric, oligomeric or polymeric silanes or other components bearing reactive silyl groups, and also materials which go on or cure in accordance with another mechanism, such as, for example, acrylates, epoxides, isocyanates, carboxylates, hydroxides, lactones, lactams, and so on. It is also possible for two or more of the silyl polyethers 1 to be used as a mixture with one another.

The particles to be modified, of various origin, various size and particle-size distribution, and of various morphology (spherical, platelet-shaped (with different aspect ratios), fibrous, fractally aggregated, cubic or cuboid, and so on) and different agglomeration states include, for example, oxidic particles, such as fumed silica, examples being AEROSIL®s from EVONIK Degussa GmbH, precipitated silicas, for example SIPERNAT®s from EVONIK Degussa GmbH, quartz particles and other inorganic oxide particles, such as glass particles, titanium dioxide, such as, for example, AEROXIDE® $TiO_2$ P25 and AEROXIDE® $TiO_2$ P90 from EVONIK Degussa GmbH, aluminium oxide, such as, for example, AEROXIDE® Alu C from EVONIK Degussa GmbH, zirconium dioxide and/or cerium dioxide, iron oxide, copper oxides, and so on, silicatic particles such as, for example, particles of kaolin, wollastonite, talc, mica, feldspars and so on, hydroxides such as aluminium trihydroxide and/or magnesium dihydroxide, boehmite, hydrotalcite and hydroxydic iron pigments, such as, for example, FeO(OH), carbonates, such as, for example, calcium carbonate and/or dolomite, metals such as iron, copper, zinc, nickel, aluminium, magnesium, and so on, metal alloys and/or carbon-containing materials, such as, for example, graphite and/or carbon black, and so on.

Organic particulate substrates which can be used are particles made, for example, of silicone resins, organically modified silicones, organic polymers and/or biopolymers, organic polyelectrolytes, melamine cyanurate, and so on.

The different particles may also be surface-modified in a mixture.

The ratio of particle mass to surface modifier is dependent on the accessible particle surface area, the desired degree of modification and the molecular weight of the modifying agent. Relative to the mass of the particles to be modified, the modifying agent of the invention may be present in a mass ratio of particle mass:modifier mass in the range from 1:10 to 1 000 000:1, preferably from 1:1 to 10 000:1 and with particular preference in the range from 2:1 to 1000:1.

Considering the particle weight in relation to the overall mixture used for the surface modification, consisting of compositions comprising the silyl polyether or polyethers 1, optionally catalyst, solvents, further silane compounds, and other auxiliaries, the mass ratio of particle weight:modifying mixture may be situated in the range from 1:1000 to 100 000:1, preferably in the range from 1:100 to 1.000:1, more preferably in the range of 2:1 to 1000:1.

Macroscopic surfaces may likewise be coated with the silyl polyethers 1 by the methods known from the prior art. In that case the silyl polyethers 1 can be used either in pure form or else in a blend with further components, examples being inorganic and/or organic solvents, reactive components such as monomeric, oligomeric or polymeric silanes, acrylates, epoxides, hydroxy compounds, amines and so on, and also further coating components or auxiliaries, for surface modification.

The silyl polyethers 1 may be applied in pure form, in organic or inorganic solvents, as aqueous emulsions, as mixtures of the silyl polyethers 1 with monomeric silanes of the formula (2) and/or other polymers which carry silyl groups, in combination with differently functionalized modifiers such as, for example, epoxides, acrylates, amines and/or other polymers.

The modification of macroscopic surfaces with the materials described may be implemented using, for example, the methods known from the prior art, such as dip, spray or spin coating, flow coating, atomizing, brush application, roller application, printed application, screen printing, stamping application and also—given appropriate consistency of the formulas of the invention that are used for surface modification—by powder coating methods as well. It is also possible, furthermore, to use emulsions of the silyl polyethers 1 in suitable organic and/or inorganic solvents to modify the surfaces, optionally with addition to said emulsions of further substances such as, for example, coating components, auxiliaries such as, for example, wetting agents, emulsifiers and/or rheological additives, and also fillers and/or functional particles.

Examples of such surfaces are macroscopic and microscopic surfaces such as surfaces of glass, coatings, metals, semiconductor materials, oxidic materials such as stones, concretes or mortars, would, organic and inorganic fibres, woven fabrics and particles, polymers, biopolymers and so on.

As catalysts for the chemical fixing of the silyl polyethers 1 on particle surface and on macroscopic surface it is possible to use the known polyurethanization, allophanatization or biuretization catalysts which are known per se to the skilled person, and the catalysts known from the literature and used typically in the hydrolysis and condensation of alkoxysilanes. These catalysts include compounds such as, for example, the zinc salts zinc octoate, zinc acetylacetonate and zinc(II) ethyl caproate, or tetraalkylammonium compounds, such as N,N,N-trimethyl-N-2-hydroxypropylammonium hydroxide, N,N,N-trimethyl-N-2-hydroxypropylammonium 2-ethylhexanoate or cholin 2-ethylhexanoate. Preference is given to the use of zinc octoate (zinc(II) ethylhexanoate) and the tetraalkylammonium compounds, more preferably to the use of zinc octoate. As catalysts it is possible, furthermore, to use the organotin compounds that are typically used, such as, for example, dibutyltin dilaurate, dioctyltin dilaurate, dibutyltin diacetylacetonate, dibutyltin diacetate or dibutyltin dioctoate, etc. In addition it is also possible to use bismuth catalysts, an example being the Bor-chi catalyst, titanium compounds, such as titanium(IV) isopropoxide or titanyl acetylacetonate, iron(III) compounds, such as iron(III) acetylacetonate, aluminium compounds, such as aluminium triisopropoxide, aluminium tri-sec-butoxide and other alkoxides, and also aluminium acetylacetonate, calcium compounds, such as calcium disodium ethylenediaminetetraacetate or calcium diacetylacetonate, or else amines, examples being triethylamine, tributylamine, 1,4-diazabicyclo[2.2.2]octane, 1,8-diazabicyclo[5.4.0]undec-7-ene, 1,5-diazabicyclo[4.3.0]non-5-ene, N,N-bis-(N,N-dimethyl-2-aminoethyl)methylamine, N,N-dimethylcyclohexylamine, N,N-dimethylphenylamine, N-ethylmorpholine etc. Organic or inorganic Brönsted acids as well, such as acetic acid, trifluoroacetic acid, methanesulphonic acid, p-toluenesulphonic acid or benzoyl chloride, hydrochloric acid, phosphoric acid, the monoesters and/or diesters thereof, such as butyl phosphate, (iso)propyl phosphate, dibutyl phosphate, etc., are suitable catalysts. Combinations of two or more catalysts can of course also be used.

The compositions of the invention comprising the curable modifiers may also comprise what are called photolatent bases as catalysts, as are described in WO 2005/100482. Photolatent bases are preferably organic bases having one or more basic nitrogen atoms, which to start with are present in a blocked form and release the basic form only after irradiation with UV light, visible light or IR radiation, as a result of scission of the molecule.

The catalyst or photolatent base is used in amounts of 0.001 to 10.0%, preferably 0.01 to 1.0% and more preferably 0.05% to 0.5%, by weight, based on the alkoxysilyl-functional silyl polyethers 1. The catalyst or photolatent base may be added in one portion or else in portions or else continuously. It is preferred to add the total amount in one portion.

As further components the mixtures may preferably comprise other, usually monomeric, silanes, hydroxyl-bearing siloxanes or solvents.

As other silanes it is possible in this case to make use in principle of all silanes, preferably those having hydrolysable alkoxy groups, and more particularly those compounds as in formula (2) and also those which are described in DE 10 2006 054155 or in WO 2005/003201 (US 2007-167598).

Furthermore, the mixtures may also comprise auxiliaries that are known per se, such as water scavengers other than the components, or further adhesion promoters and/or reactive diluents, and also plasticizers, examples being phthalates, benzoates, phosphate plasticizers, thixotropic agents, fungicides, flame retardants, pigments, etc. In addition, light stabilizers, antioxidants, free-radical scavengers and other stabilizers may be added to the mixtures.

The mixtures may comprise organic substances, preferably liquids and solvents. The solvents in this case serve, for example, to lower the viscosity of the uncrosslinked mixtures and promote adherence to the particle surface. Suitable solvents include in principle all solvents and also solvent mixtures. Preferred examples of such solvents are ethers such as tert-butyl methyl ether, esters, such as ethyl acetate or butyl acetate or diethyl carbonate, and alcohols, such as methanol, ethanol and the various regioisomers of propanol and butanol, or else glycol types selected in accordance with the specific application. Moreover, aromatic and/or aliphatic solvents can be used, and also halogenated solvents, such as dichloromethane, chloroform, tetrachloromethane, hydrofluorocarbons (FREON), and so on, but also inorganic solvents such as, for example, water, $CS_2$, supercritical $CO_2$, and so on.

The possibilities for application of surfaces, or particle surfaces, modified in this way are diverse. For instance, particles treated in this way may be used, for example, as fillers for polymers or for the production of polymer compounds, nanocomposites and masterbatches. A good overview of functional fillers and polymers is offered by "Functional Fillers for Plastics", edited by Prof. Dr. Marino Xanthos, WILEY-VCH Verlag GmbH & Co. KgaA, Weinheim, 2005, ISBN 3-527-31054-1. The use of the silyl polyethers of the invention may be such that, on the one hand, the particles for modification are modified in an operation beforehand and then dispersed in the polymer, though secondly it is also possible for the silyl polyethers 1 to be added when the fillers are dispersed in the respective polymer, by way, for example, of a liquid feed to the extruder, with an effective dispersing section following. Surprisingly, in general, the modification of particle surfaces with the silyl polyethers 1 is accomplished successfully without caking or aggregation of the particulate materials to be modified, in spite of the polyfunctional character of the silyl polyethers 1. Furthermore, particles surface-modified in accordance with the invention may be used, for example, as fillers or functional additives in coating materials, polymeric foams, organic resins or silicone resins, where appropriate with reactive attachment to the respective matrices, as melt flow index improvers in injection moulding applications, for obtaining physical effects on surfaces, such as superhydrophobicity, temperature-dependent wettability, beading effects, influencing the dirt pick-up behaviour and the soil release behaviour on solid surfaces on construction, textiles or fibres, and also the adhesion of condensates and ice to surfaces and particles bearing the coatings of the invention, and as slip additives or lubricants, in sealing systems, for obtaining haptic effects, such as a silky hand (soft-touch surfaces), for example, or a defined surface grip or roughness, as matting agents, as points of attachment for other materials, such as other coating materials, for example, as adsorbents or absorbents in, for example, paper materials or filter materials or fabrics, as self-dispersible particles for producing dispersions, as particulate emulsifiers (for what are called "Pickering emulsions", see also "emulsions", Spencer Umfreville Pickering, Journal of the Chemical Society, Transactions (1907), 91, 2001-2021), as reactive and/or crosslinkable particles, where appropriate in dispersion in liquid media, as active components in defoamers, in architectural preservatives, for example as active components for integral hydrophobization of materials, as a structured hydrophobic component for surface hydrophobization or as a carrier for active liquid components, as (optionally reactive) encapsulants, such as, for example, for core-shell particles or for the microencapsulation of liquid systems, for the modification of membrane materials, as for example for obtaining a defined, adjustable porosity, selectivity or permeability, as antistatic additives, for example after hydrophilic or hygroscopic particle surface modification, as free-flow aids, as additives for obtaining or enhancing scratch resistance on the part of the surfaces or materials furnished with the particles, or as particulate additives with other functions, for example as microbicidal additives, as fluorescent labels or as effect pigments, as release agents, as constituents of cable coatings with low-temperature resistant properties, as manufacturing components of rubber parts and membranes, as a size or ingredients for sizes in the textile and glass fibre industries, for paper, as additives for toners, as abrasives or line fillers in cosmetics, as carrier materials or formulating ingredients which release auxiliaries or active substances over a prolonged period of time, the substances which may be present in the particles and are to be released being, for example, cosmetic oils and active substances, fragrances, active pharmaceutical substances, active antimicrobial substances, including, for example, silver and compounds containing silver, and also dyes and preservatives and so on.

The invention accordingly further provides the materials, fabrics and surfaces mentioned above that are coated and are produced using the compositions comprising the silyl polyethers (1), (5) and/or (6). These polyethers of the formula (1), bearing reactive alkoxysilyl groups, can be used for surface modification or as a coating, as a bulk material and also, as a result of suspension polymerization, for example, for producing particulate materials. Their crosslinking to form solid thermoset end products and their fixing to substrates comprising reactive groups, more particularly hydroxyl groups, is accomplished in a simple way in the presence of water and optionally with addition of acid or base or other accelerators, it being possible for the cure rate to be controlled by raising the temperature during the curing operation. The polymer architecture of these crosslinkable polyethers may be varied in a wide variety of ways in accordance with the nature of the initiator and also the nature, amount and sequence of the epoxide monomers that can be employed, in order thus to tailor important performance product properties as a function of the particular end use. Thus, for example, by varying the fraction of alkoxysilane units in the polymer chain, it is possible to influence within wide limits the crosslinking density and hence the mechanical and physicochemical properties profile of the cured polymers and of the surfaces provided therewith and/or of the particles on whose surface they are anchored. Here, surprisingly, even silyl polyethers 1 furnished with a considerable density of alkoxysilyl functionalization are low-viscosity liquids with good handling properties, and so, even in the case where the target coatings are highly crosslinked coatings with good adhesion, there are no restrictions whatsoever on the level at which this component is added.

This finding differentiates the teaching of the invention from the procedure set out in DE 10 2006 054155, which is geared to the introduction of free silane monomers as formulating constituents in the final formulas, in order to ensure that the necessary crosslinking density is obtained in conjunction with a low processing viscosity. The alkoxysilyl-containing silyl polyethers 1, which have virtually no limits on their structural diversity, open up, for the person skilled in the art of polymer chemistry, a level of design freedom, through the incorporation, for example, of ester, carbonate and aromatic structural elements, that addresses virtually any performance requirements.

The silyl polyethers 1 described in the as yet unprepublished specification DE 10 2008 000360.3, and preferably those compounds which carry more than one silyl group per hydroxyl group, are suitable for the particularly uniform and firmly adhering surface modification of inorganic and organic surfaces, particle surfaces and/or pore surfaces. A further possible advantage is that gelling and/or bridging occur with self-crosslinking of the prepolymers.

This is possible owing, among other things, to the low viscosity of the silyl polyethers 1 as alkoxysilyl prepolymers and to their high reactivity with respect to the surfaces that are to be modified.

This permits modification of a very wide variety of surfaces, consisting for example of metal oxides, mixed oxides, nitrides, hydroxides, carbides, carbonates, silicates, pigments, carbon blacks, elements or alloys, and also surfaces of organic materials. Furthermore, of course, the surfaces of organic particles are accessible to surface modification as well, such as those of silicone resins, organically modified silicones, organic polymers or biopolymers.

Hence, the silyl polyethers 1 may be employed, for example, as base materials for the preparation of adhesives, as reactive crosslinkers, as adhesion promoters and primers, and also binders for metals, glass and glass fibres/glass fabrics, wood, wood-based materials, natural fibres, for the finishing and treatment of optionally textile planar structures and fibres made from natural and/or synthetic raw materials and also mineral raw materials and also, for example, of cork, leather, paper, tissue and silicatic and oxidic materials.

The incorporation of the alkoxysilyl moieties, which become anchored via hydrolytic processes to masonry, concrete, mortar, etc., proves to be extremely advantageous in the context of the use of systems thus equipped in the area of the building industry, where the aim is for the connecting and insulating sealing of, for example, frames for windows and doors in structural shells.

The invention further provides for the water repellency treatment of buildings through use of hydrophobizing compositions comprising silyl polyethers 1, and the hydrophobicity of the surface that is ensured thereby, depending on end application, and can be set in a targeted way, this hydrophobicity helping on the one hand to prevent the surface from becoming saturated with moisture but on the other hand allowing water vapour to pass through.

Particularly in the case of polyethers of the formula 1 with a hydrophobic radical or else a high PO, BO or SO content (propylene oxide, butylene oxide and/or styrene oxide content), it is possible to achieve high rates of hydrophobization. SO-containing polyethers in particular are highly suitable, for example, for modifying carbon materials, such as graphite and/or carbon black, for example, and accordingly these materials are easier to disperse, for example.

The equipping or treatment of the planar structures serves on the one hand to protect the surface or fibre, to improve and/or alter its properties or to obtain new profiles of properties.

Thus, for example, graphite and also hexagonal boron nitride can be incorporated into a silyl polyether 1 in order to produce what are called low-friction coatings. These low-friction coatings have "smoothness" as a haptic effect, in contrast, for example, to coatings filled with AEROSIL® 200, which appear very "grippy".

The invention further provides the tribological and/or haptic coatings produced in this way, comprising graphite or boron nitride.

The invention additionally provides sealants and/or adhesives comprising the silyl polyethers 1, where even a surface coating is itself already capable of providing sealing or adhesive bonding. These sealants and/or adhesives may comprise, in particular, lubricant additives and also, for example, $MoS_2$ or PTFE particles.

Furthermore, the silyl polyethers 1 may also find use in the production of electrical and/or electronic components such as, for example, OLEDs and solar panels. As additives in this case there may be conductive particles or ionic liquids present, hence allowing use in conductive coatings and conductive adhesives, in conductor tracks for example, for contacting and/or for antistatic coating.

The silyl polyethers 1 may be utilized alone or as additives in aqueous systems for the treatment of the stated planar structures and fibres, and thus allow the use of the planar structures and fibres thus treated in the hygiene, medical, construction, automotive, home furnishing, textile apparel, sport and agricultural sectors.

The particles or planar structures thus surface-modified therefore have new properties or optimized properties such as in respect, for example, of softness, lubricity, water transport/absorption, water/oil repellency, UV protection, self-cleaning (Lotus effect) for awnings, for example, flame retardancy, an increase in strength in tandem with excellent flexibility, antistatic properties and resistance to bacteria, viruses and chemicals.

The invention further provides for the use of the silyl polyether 1 formulations, for example, in cosmetic applications as well, as additives in varnish or nail-varnish formulations.

A modern nail varnish or nail coating composition serves to provide an appealing form and colouring to fingernails and toenails. In addition the nail is protected from environmental influences and the hardening of the nail bed or nail surface is ensured. Particular efforts are undertaken in order to provide nail varnish coatings which are long-lasting, insensitive to scratching and splitting, lustrous and in attractive colours and brilliance. Nail varnishes (therefore) contain a large number of very different ingredients, of which the particularly important ones are film formers, adhesion promoters, plasticizers, solvents and pigments. Pyrogenic or fumed silica is used as a rheological and thixotropic modifier. U.S. Pat. No. 4,873,077, GB 1177420 and DE 69111621 (U.S. Pat. No. 5,330,750) describe a multiplicity of additives for ensuring good load-bearing resistance, effective split prevention, the breaking and tearing of the nails, and a long life for the nail varnish after drying, as a flexible, well-adhering, hard film on the nail.

With the silyl polyethers 1 it is also possible, furthermore, to bring about specifically physical effects on solid substrates, such as hydrophobic or hydrophilic surface properties, for example. In this context it is also possible, furthermore, for effects of this kind to be subject to an additional stimulus, such as that of the prevailing temperature, for example. As is known from the literature, polyethers in water have what are called cloud points, as a function of temperature, which result from the development with increasing temperature of incompatibility with the surrounding medium. It has been shown that it is possible, via the attachment of silyl-modified polyether chains to different surfaces, to make their contact angles with respect to various liquids, water for example, a function of temperature.

In the context of increasing environmental awareness, the addition of organic solvents for the purpose of lowering the viscosity of formulations for the modification of surfaces has in recent years, however, become increasingly a subject of criticism. An alternative is to apply the prepolymers of the invention in the form of an emulsion, advantageously an aqueous emulsion. Emulsions comprising silyl-functionalized prepolymers have been described in the literature. In the specification DE 2558653 (U.S. Pat. No. 3,941,733), Chang describes emulsions of self-emulsifying, silyl-bearing polyurethanes and their use for the coating of surfaces. In the specification U.S. Pat. No. 4,376,149, Martin describes emulsified mixtures of OH-siloxanes and polyethers which are silylated at the chain ends, and their use for the coating of textiles. Klauck, Maier and Berthauer, in the specification DE 4215648, describe storage-stable contact adhesives based on solutions or emulsions of cationically modified, alkoxysilane-terminated polyurethanes. U.S. Pat. Nos. 6,713,558 and 6,831,128 describe water-thinnable emulsions of silylated elastomers and their preparation, while WO 2007/072189 (US 2008-0275176) and WO 2008/090458 describe emulsions of polymers bearing silyl groups.

A further application of the compounds of the formula (1) bearing alkoxysilyl groups is as aqueous emulsions. Emulsifiers contemplated for such emulsions are in principle all anionic, non-ionic, cationic and amphoteric emulsifiers, and also mixtures of emulsifiers. Preferred examples of such emulsifiers are alcohol ethoxylates, fatty acid ethoxylates, ethoxylated esters and (ethoxylated) sorbitan esters.

The aqueous phase of the emulsions may comprise hydrophilic, inorganic fillers for the purpose of modifying the mechanical properties of the coatings of the invention, with the proviso that these hydrophilic fillers are added subsequently to the already-stabilized emulsion. It can be advantageous if the surface of the fillers employed has at least one functional group, so that after drying or breaking of the emulsion, chemical reactions occur between reactive functional groups of the silyl polyether 1 and those on the filler surface.

Examples of such fillers are fumed and precipitated silicas, inorganic oxides such as aluminium oxide, titanium dioxide and zirconium dioxide, glass and quartz, hydroxides such as aluminium hydroxide and magnesium hydroxide, silicates such as wollastonite, mica, kaolin and talc, calcium carbonate and other carbonates, metals such as copper, zinc and nickel, and metal alloys, and also graphite and carbon black.

Furthermore, the emulsion may comprise organofunctional and water-insoluble silanes of low molecular weight, as described above. The emulsion may likewise comprise the above-described catalysts for the binding of the silyl polyethers 1 to a surface.

The emulsions may also be admixed with further functional substances. Examples of these include rheological additives, defoamers, deaerating agents, film-forming polymers, antimicrobial substances and preservatives, antioxidants, dyes, colourants and pigments, anti-freeze agents, fungicides, adhesion promoters and/or reactive diluents, and also plasticizers and complexing agents. Spraying assistants, wetting agents, vitamins, growth substances, hormones, fragrances, light stabilizers, free-radical scavengers, UV absorbers and also further stabilizers as well may be added to the mixtures.

The invention further provides the production of flame-retardant thermoplastic polymer compounds or thermoset moulding compounds comprising silyl ethers 1 and able additionally to comprise flame-preventing and/or flame retardant substances such as, for example, ATH (aluminium trihydrate=aluminium hydroxide=aluminium trihydroxide), MDH (magnesium dihydroxide) or melamine cyanurate. Polymer compounds of this kind are employed, for example, for producing cable insulation materials based on polypropylene, polyethylene or ethylene-vinyl acetate for cables and cable jackets, or flame-preventing partitions are produced on the basis of polypropylene, for example, which in public buildings such as sports halls, for example, are subject to particularly stringent requirements.

The flame retardant compositions, compounds or electrical cables thus treated may have an improved mechanical stability, improved dispersing of further additives, good extrusion properties, even in the case of a high level of filling with particulate additives (as for example with talc, calcium carbonate, etc.) and also improved flame prevention, or reduced smoke evolution, under strong heating. Particularly when silyl polyethers are used that contain siloxane groups, the silicon content may provide additional stability in the event of fire, since, after combustion, an additionally stabilizing and fire-retardant $SiO_2$ component is left. Furthermore, even during combustion, the phenomenon known as skinning is forced to occur at an earlier point in time, and reduces the further increase in the temperature of the material, hence inhibiting the progress of the fire, a factor which is particularly relevant in the case, for example, of cables which lead from one room into the next room. Additionally provided by the invention are composites such as, for example, wood-plastic composites (WPCs) produced using the silyl polyethers 1. WPCs are thermoplastically processable composites which are composed of different proportions of wood, plastics and additives and are processed by thermoplastic shaping techniques, such as, for example, extrusion, injection or compression moulding techniques. As compared with polypropylene-maleic anhydride-grafted copolymers, the innovative silyl polyether composites exhibit enhanced attachment to the wood or fibre substructure of these composites. The silyl polyethers 1 bind to the fibres based on wood, coconut or other naturally available fibre products and at the same time render this surface water repellent, thereby guaranteeing a reduced drying time of the wood fibre pellets (energy saving). In contrast to conventional inorganic fillers, even low molecular mass products may develop a very good compatibilizing effect here, since, in the case of rapid extrusion operations, they can be homogeneously dispersed much more rapidly, in seconds, than the PP-MAA polymers.

The invention further provides powder coating curing agents with defined glycidyl functionality and improved compatibility and/or adhesion (adhesion promotion) to the substrate, which is also supported by improved adhesion and which reduces the sub-film corrosion creep in powder coated façade applications. The promotion of adhesion is of key significance in particular in the case of oxidic or silicatic surfaces such as mortar, screeding or cement, for example.

The invention further provides liquid pastes in which the silyl polyethers of the formula 1 are used alone instead, for example, of a customary polyether polyol (PPG 1000), which generally necessitates the additional use of a dispersant, since the silyl polyether of the formula 1 combines the properties of both materials. Pastes of this kind which may comprise pigments as colourants or may further comprise dyes and other additives are used for the colouring of polyol-based systems such as, for example, PU foams, thermoplastic urethanes or the like.

Another embodiment of the invention relates to reactive diluents, emulsions, wetting agents, paints, adhesion promoters, plasticizers, thixotropic agents, fungicides, flame retardants, pigments, fillers, polymeric foams, organic resins or silicone resins, melt-flow-index improvers, constructions, textiles or fibres, slip additives, lubricants, matting agents, adsorbents or absorbents, self-dispersible particles, particulate emulsifiers, defoamers, architectural preservatives, encapsulants, in sealing systems, antistatic additives, freeflow aids, microbicidal additives, fluorescent markers, effect pigments, release agents, low-temperature-resistant cable coatings, conductive coatings, conductor tracks, antistatic coatings, electronic and/or electrical components, rubber parts and membranes, size in the textile and glass fibre industries, paper, additives for toners, abrasives or line fillers in cosmetics, formulating agents or carrier materials, dyes and preservatives, coatings, corrosion inhibitors, inks, tribological and/or haptic coatings, coated and/or modified with a composition according to the invention.

Another embodiment of the invention is the use of the planar structures, particles and/or fibres provided with surface modification according to invention in the hygiene, medical, cosmetological, construction, automotive, home furnishing, apparel textile, sports and/or agriculture sector.

Another embodiment of the invention is the use of the silyl polyether compositions according to the invention in cosmetic applications as additives in lacquer or nail varnish formulations, for imparting water repellency to constructions, as sealants and/or adhesives, flame retardants, cable jackets, composite materials, powder coating hardeners and/or liquid pastes.

Additional subject matter of the invention will be apparent from the claims, the entire disclosure content of which is part of the description.

BRIEF DESCRIPTION OF THE DRAWINGS

The subject matter of the present invention is illustrated by, but not confined to, FIGS. 1 to 3.

Figure 1:
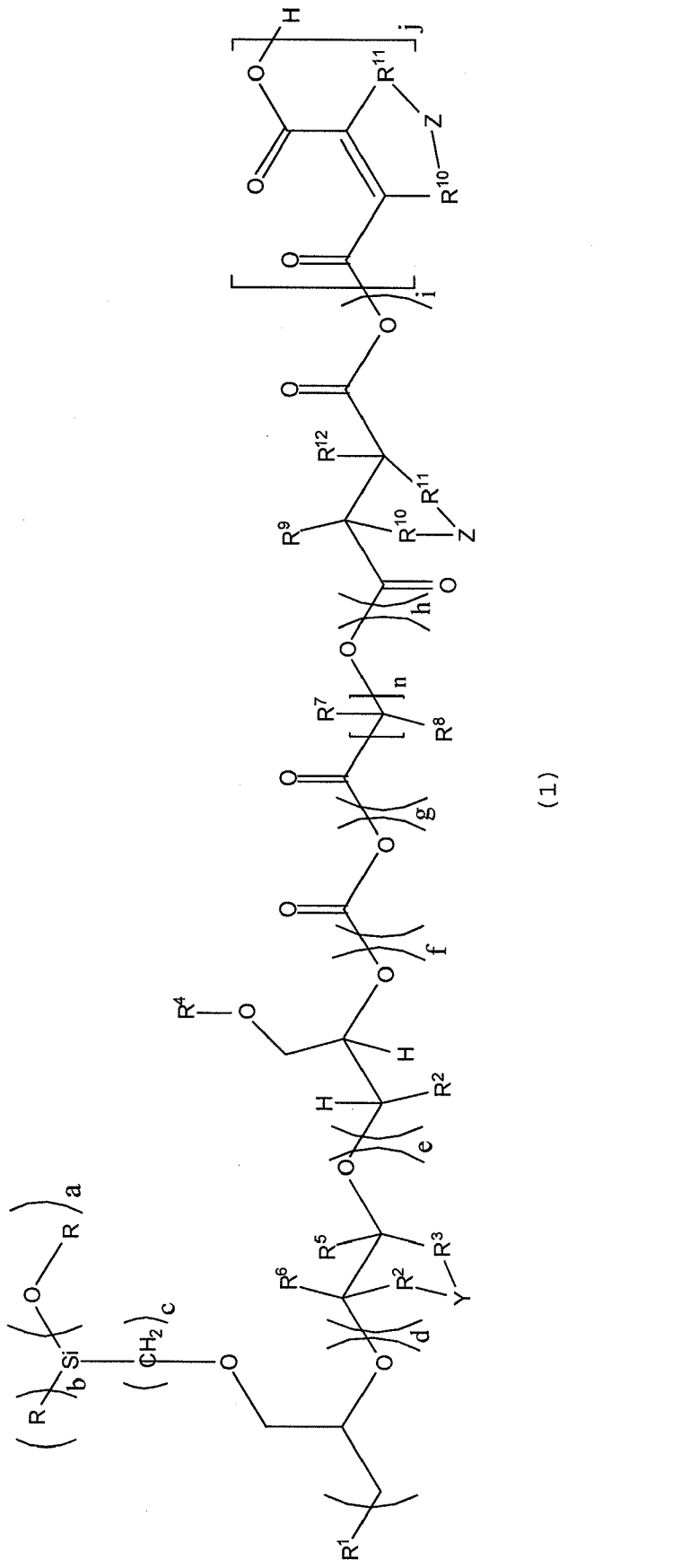
FIG. 1 shows the formula (1a).

The examples given below provide an exemplary description of the present invention, without any intention that the invention, the breadth of whose application is given by the description as a whole and by the claims, should be confined to the embodiments specified in the examples.

Unless explicitly stated otherwise, in the present description and the examples which follow, all quantitative and percentage data are given by weight, all pressures are 0.10 MPa (abs.) and all temperatures are 20° C.

Abbreviations: PO=propylene oxide, EO=ethylene oxide

At various points the tack-free time is reported as a measure of the reactivities of the silyl polyethers 1. The tack-free time is the time which elapses from the delivery of the silyl polyether 1 to the air until the polymer surface has cured to an extent such that, when this surface is contacted with a pencil or the finger, there is neither sticking of polymer material thereto or any incidence of stringing.

EXPERIMENTAL SECTION

The invention is further described by the following non-limiting examples which further illustrate the invention, and are not intended, nor should they be interpreted to, limit the scope of the invention.

In the examples below, the following trialkoxysilyl-containing silyl polyethers 1 were used, which were prepared in accordance with the yet as unpublished specification DE 10 2008 000360.3 on the process principle of the DMC-catalysed alkoxylation of 3-glycidyloxypropyltriethoxysilane (Dynasylan® GLYEO) from Evonik Degussa GmbH or 3-glycidyloxypropyltrimethoxysilane (Dynasylan® GLYMO) from Evonik Degussa GmbH.

Trialkoxysilyl Polyether SP-1

Low molecular mass, virtually colourless, low-viscosity polyether of blockwise structure, prepared starting from octanol, having an average molar mass of approximately 3000 g/mol and seven-fold trialkoxysilane functionality.

Chemical structure according to monomer addition: 1-octanol+8 mol PO+3.5 mol GLYEO+8 mol PO+3.5 mol GLYEO+2 mol PO Epoxide oxygen content <0.05%, OH number 19.5 mg KOH/g, viscosity (25.0° C.): 0.19 Pa·s Trialkoxysilyl Polyether SP-2

Low molecular mass, virtually colourless, low-viscosity polyether of largely random structure, prepared starting from octanol, having an average molar mass of approximately 3000 g/mol and seven-fold trialkoxysilane functionality.

Chemical structure according to monomer addition: 1-octanol+8 mol PO+(7 mol GLYEO/10 mol PO)

Epoxide oxygen content <0.05%, $M_w$ by GPC 2760 g/mol, viscosity (25.0° C.): 0.15 Pa·s Trialkoxysilyl Polyether SP-3

Low molecular mass, virtually colourless, low-viscosity polyether of largely random structure, prepared starting from octanol, having an average molar mass of approximately 3000 g/mol and four-fold trialkoxysilane functionality.

Chemical structure according to monomer addition: 1-octanol+2 mol PO+(4 mol GLYEO/26 mol PO/8.5 mol EO)+2 mol PO Epoxide oxygen content <0.05%, OH number 22.0 mg KOH/g, viscosity (25.0° C.): 3.18 Pa·s Trialkoxysilyl Polyether SP-4

Low molecular mass, virtually colourless, low-viscosity polyether of blockwise structure, prepared starting from octanol, having an average molar mass of approximately 3000 g/mol and seven-fold trialkoxysilane functionality. Chemical structure according to monomer addition: 1-octanol+2 mol PO+(3 mol PO/3 mol EO)+3.5 mol GLYEO+(5 mol PO/3 mol EO)+3.5 mol GLYEO+2 mol PO Epoxide oxygen content <0.05%, OH number 20.0 mg KOH/g, viscosity (25.0° C.): 0.16 Pa·s Trialkoxysilyl Polyether SP-5

Low molecular mass, virtually colourless, low-viscosity polyether of blockwise structure, prepared starting from octanol, having an average molar mass of approximately 2400 g/mol and 1.5-fold trialkoxysilane functionality. Chemical structure according to monomer addition: 1-octanol+30 mol PO+1.5 mol GLYMO+3 mol PO Epoxide oxygen content <0.05%, $M_w$ by GPC 2650 g/mol, OH number 22.0 mg KOH/g viscosity (25.0° C.): 0.32 Pa·s Trialkoxysilyl Polyether SP-6

Low molecular mass, virtually colourless, low-viscosity polyether of blockwise structure, prepared starting from octanol, having an average molar mass of approximately 3000 g/mol and six-fold trialkoxysilane functionality. Chemical structure according to monomer addition: 1-octanol+4 mol PO+3 mol GLYEO+10 mol PO+3 mol GLYEO+10 mol PO Epoxide oxygen content <0.050, OH number 24.0 mg KOH/g, viscosity (25.0° C.): 0.16 Pa·s Trialkoxysilyl Polyether SP-7

Low molecular mass, virtually colourless, low-viscosity polyether of blockwise structure, prepared starting from octanol, having an average molar mass of approximately 2200 g/mol and single-fold trialkoxysilane functionality. Chemical structure according to monomer addition: 1-octanol+2 mol PO+1 mol GLYMO+30 mol PO Epoxide oxygen content <0.05%, OH number 27.5 mg KOH/g, viscosity (25.0° C.): 0.32 Pa·s Trialkoxysilyl Polyether SP-8

High molecular mass, virtually colourless polyether of random structure, prepared starting from polyetherol, having an average molar mass of approximately 8200 g/mol and eight-fold trialkoxysilane functionality.

Chemical structure according to monomer addition: Polypropylene glycol monobutyl ether (on average 520 g/mol)+(8 mol GLYEO/94 mol PO)

Epoxide oxygen content <0.03%, OH number 7.6 mg KOH/g, viscosity (25.0° C.): 1.68 Pa·s Trialkoxysilyl Polyether SP-9

Low molecular mass, virtually colourless, polyether, prepared starting from 1-octanol, having an average molar mass of approximately 2300 g/mol and single-fold trialkoxysilane functionality.

Chemical structure according to monomer addition: 1-octanol+1 mol GLYEO+(9 mol EO/27.5 mol PO)

Epoxide oxygen content <0.05%, OH number 25.5 mg KOH/g, viscosity (25.0° C.): 0.33 Pa·s Trialkoxysilyl Polyether SP-10

Low molecular mass, virtually colourless, polyether, prepared starting from 1-octanol, having an average molar mass of approximately 2400 g/mol and single-fold trialkoxysilane functionality.

Chemical structure according to monomer addition: 1-octanol+2 mol PO+1 mol GLYMO+(9 mol EO/27.5 mol PO) Epoxide oxygen content <0.05%, OH number 25.0 mg KOH/g, viscosity (25.0° C.): 0.29 Pa·s

TABLE 1

| Example 1: Preparation of an emulsion | |
| --- | --- |
| Substances | Amount/Grams |
| TEGO ® Alkanol TD12 | 9.0 |
| Rewopal ® LA3 | 6.0 |
| Polyether SP-1 | 100.0 |
| Water | 100.0 |

9.0 g of TEGO Alkanol TD12 (isotridecyl alcohol, polyoxyethylene-(12) ether, Evonik Goldschmidt GmbH), 3.0 g of Rewopal LA3 (lauryl alcohol, polyoxyethylene-(3) ether, Evonik Goldschmidt GmbH) and 22.5 g of water were heated to 60° C. in a double-wall glass vessel and homogenized using a Mizer disc at 1000 rpm until a viscous, homogeneous paste was formed. With the aid of a dropping funnel, polyether SP-1 was incorporated dropwise into the paste over the course of 30 minutes, with stirring. The completed paste was stirred at 1000 rpm for 10 minutes. Thereafter the paste was diluted with the remaining 77.5 grams of water. This produced a low-viscosity emulsion. The size of the droplets was measured by means of dynamic light scattering (Malvern HPPS with 633 nm HeNe laser). Evaluation of the correlation function using the CONTIN algorithm indicated a monomodal droplet size distribution with an average droplet radius of 135 nm.

Example 2

Coating (1)

Using a transfer pipette (Brand), 1.00 ml of dibutyltin diacetylacetonate (DBTAA) was added to 50 ml of the emulsion described in Example 1. The DBTAA was dispersed in the emulsion with stirring at 1000 rpm using a Mizer disc. A glass plate was cleaned, rinsed with isopropanol and dried. With the aid of a doctor blade, a film of emulsion 150 micrometers thick was casted onto the cleaned glass plate. The drawn emulsion film was dried at room temperature and cured.

Example 3

Coating (2)

Using a transfer pipette (Brand), 1.00 ml of dibutyltin diacetylacetonate (DBTAA) was added to 50 ml of polyether SP-1. The DBTAA was dispersed in the prepolymer by stirring at 1000 rpm using a Mizer disc. A glass plate was cleaned, rinsed with isopropanol and dried. With the aid of a doctor blade, a film of prepolymer 150 micrometers thick was casted onto the cleaned glass plate. The prepolymer was cured at room temperature.

Example 4

Coating (3) and Determination of Contact Angle

Using a transfer pipette (Brand), 1.0 g of dibutyltin diacetylacetonate (DBTAA) was added to a mixture of 40 g of polyether SP-2 and 10 g of Silastic Fluid DC4-2737. The mixture was homogenized by stirring at 1000 rpm using a Mizer disc. A glass plate was cleaned, rinsed with isopropanol and dried. With the aid of a doctor blade, a film of mixture 150 micrometers thick was casted onto the cleaned glass plate. The mixture was cured at room temperature. This gave a clear coating.

Figure 2:
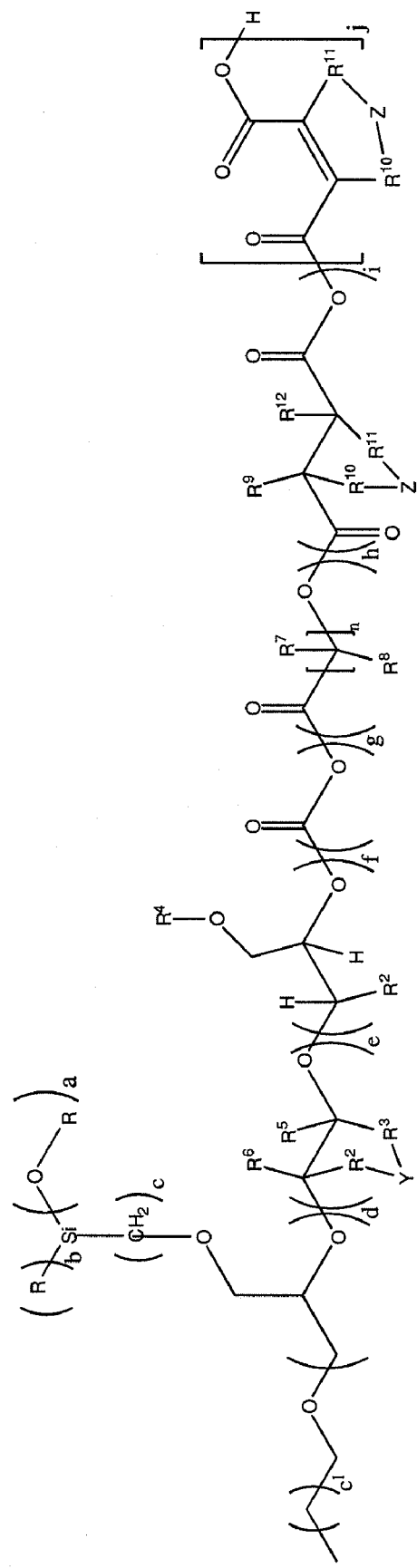
FIG. 2 shows the formula (5a).

Subsequently the contact angle of the surface coating with respect to water was determined by means of a contact angle measuring instrument OCA35 from DataPhysics Instruments GmbH. The result is shown in FIG. 2. The contact angle of both coatings with respect to water (i.e. polyether SP-2 with and without Silastic Fluid DC4-2737) decreases over time. This indicates a change in the morphology and/or chemistry of the surface on contact with water.

Example 5

Determination of Recoatability

The recoatability of the coating from Example 3 was investigated using a red flexographic ink. The ink consisted of 47% Joncryl 2647 (BASF), 10% Joncryl 61 (BASF), 38% Flexoverse Red RCD5704 (Sun Chemicals) and 5% water. Using a doctor blade machine (RK Print Coat Instruments Ltd) at speed setting 4, with a 12 µm roller doctor, the ink was applied to the cured coating from Example 3. After drying, a homogeneous coating was produced, without craters or other signs of dewetting.

Example 6

Determination of Pendulum Hardness

The pendulum hardness of the coatings from Examples 3 and 4 was determined using a pendulum damping test instrument 299/399 from Erichsen in accordance with DIN 53157. The pendulum hardness, often also referred to as pendulum damping, is a parameter which is commonplace in the coating industry for the hardness of a coating. It is determined by means of the vibration damping of a pendulum placed on the surface of a coating, the pendulum swinging back and forth on two steel balls as a bearing surface. The lower the hardness of the dry coating drawn down onto a planar surface, the greater the extent to which the swing energy of the pendulum is "damped". The parameter determined is the number of swings. The results are summarized in Table 2 below.

TABLE 2

Pendulum hardness, abrasion resistance and gloss of different coatings

| Coating | Pendulum hardness Swings | Number of rubs | Gloss 60° | 85° |
|---|---|---|---|---|
| Polyether SP-3 | 26 | 2 | 155 | 113 |
| Polyether SP-1 | 68 | 3 | 154 | 112 |
| Polyether SP-4 | 11 | 1 | 156 | 118 |
| Polyether SP-2 | 26 | 1 | 156 | 117 |
| Polyether SP-2/ Silastic, 80:20 | 68 | 1 | 126 | 103 |

Example 7

Determination of Abrasion Resistance

The abrasion resistance of the coating from Examples 3 and 4 was tested using a CM-5 Crockmeter from ATLAS Material Testing Technology GmbH. In this case a piece of abrasive material (SCOTCH-Brite CF-HP hand scouring pad S ultra fine-grey from 3M) was bonded to a rod and the rod was then rubbed over the area under test. The rubbing angle was 90°. The point in time at which visible damage to the surface became apparent was the time at which measurement was halted. The parameter determined was the number of rubs. The results are summarized in Table 2 above.

Example 8

Determination of Gloss

The gloss of the coatings from Examples 3 and 4 was tested using a REFO 3-D reflectometer from Dr. Lange GmbH. Gloss values were measured both at 60° and at 85°. The results are summarized in Table 2 above.

Example 9

Aftertreatment of Fillers by Direct Application to the Filler Surface 495 g of the fillers below were introduced into a Henschel mixer, and then 5 g of each of the non-inventive and inventive compounds were added in order to hydrophobize the filler surfaces. For this purpose the apparatus was operated at a speed of 900 rpm for 15 minutes, in the course of which there may be heating to up to 70° C. Subsequently the fillers were placed in a 100 ml measuring cylinder for determination of the differences in bulk density.

The results are given in Table 3:

TABLE 3

| Filler/pigment | Surface treatment | Fill level in ml |
|---|---|---|
| Talc HTP 1 | no addition | 15 g give 70 ml |
| | with TP 6875 | 15 g give 70 ml |
| | with silicon oil 1000 | 15 g give 75 ml |
| | with SP-5 | 15 g give 63 ml |
| | with SP-6 | 15 g give 60 ml |
| | with SP-7 | 15 g give 64 ml |
| | with SP-8 | 15 g give 68 ml |
| | with SP-1 | 15 g give 66 ml |
| ATH Apyral 40 CD | no addition | 30 g give 70 ml |
| | with TP 6875 | 30 g give 90 ml |
| | with SP-5 | 30 g give 85 ml |
| | with SP-8 | 30 g give 84 ml |
| | with SP-7 | 30 g give 82 ml |

Surprisingly it was found that the resultant bulk densities, in spite of hydrophobization with the inventive substances, do not increase when used in combination with talc, or do not increase as greatly as non-inventive substances do for ATH. Non-inventive products considered for the hydrophobization are in this case silicone oil or alkylsiloxanes (TEGOPREN® TP 6875, Evonik Goldschmidt GmbH) for purposes of comparison.

Hence it is possible to produce fillers having a relatively low bulk density (relevant for storage space and emptying in the case of silo loading), or to use the compounds of the invention to design filler surfaces which permit the filling of masterbatches and compounds with a greater consistency of weight in the extrudate, since the lower bulk density causes less bridging in the intake region of the fillers, which is relevant, for example, for filler compounds with a fill level of 60-80% with filler in various polymers such as polypropylene, for example. The lower bulk density produced by the innovative hydrophobization is economically relevant for compounders.

Figure 3:
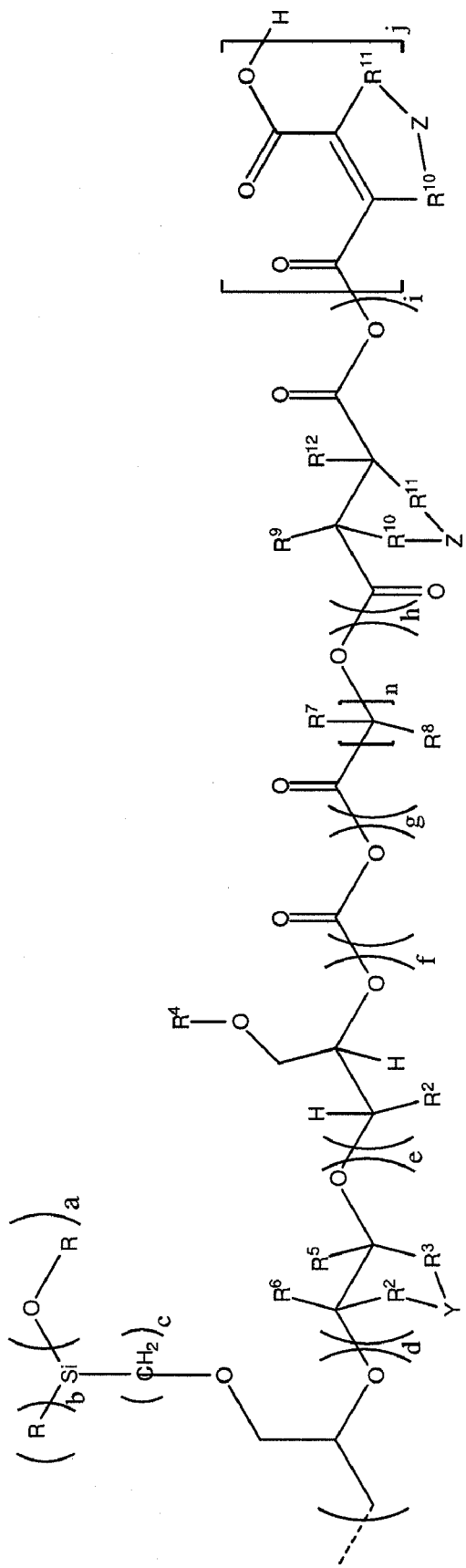
FIG. 3 shows the formula (6a).
Figure 4:
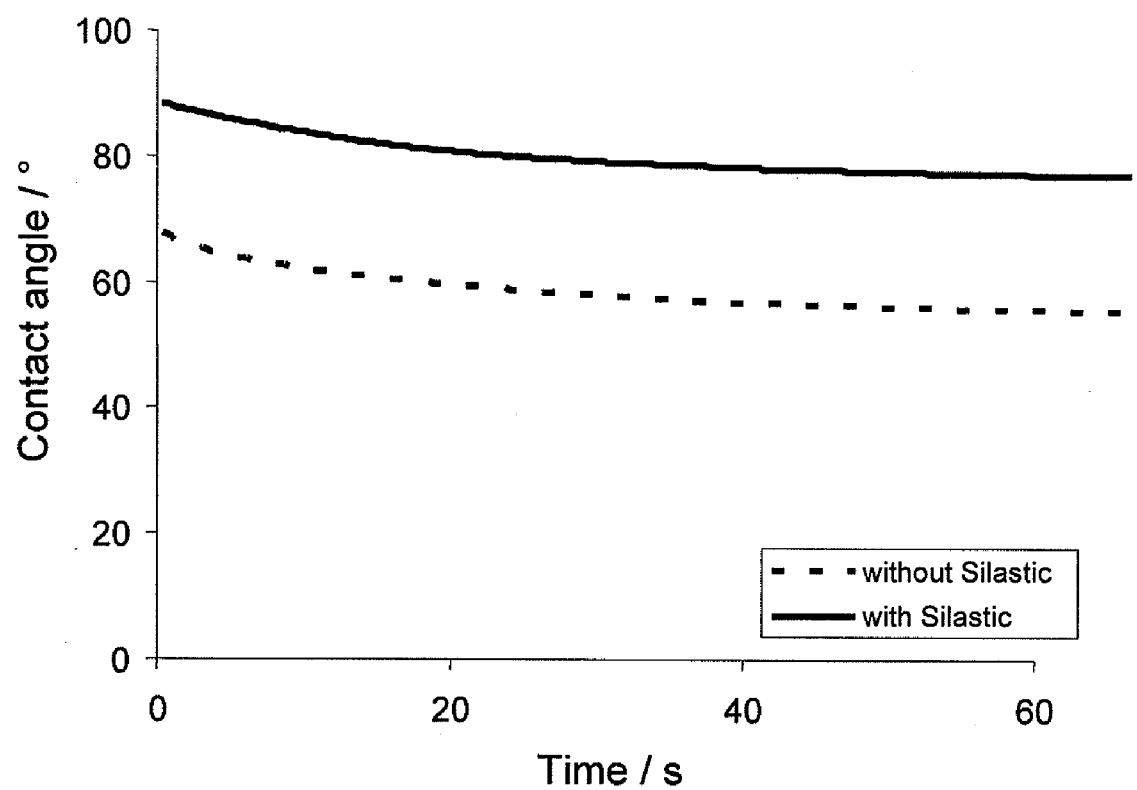
FIG. 4 shows the contact angles with respect to water of a coating based on polyether SP-2, applied both with and without Silastic Fluid DC4-2737 (Example 4).
Figure 5:
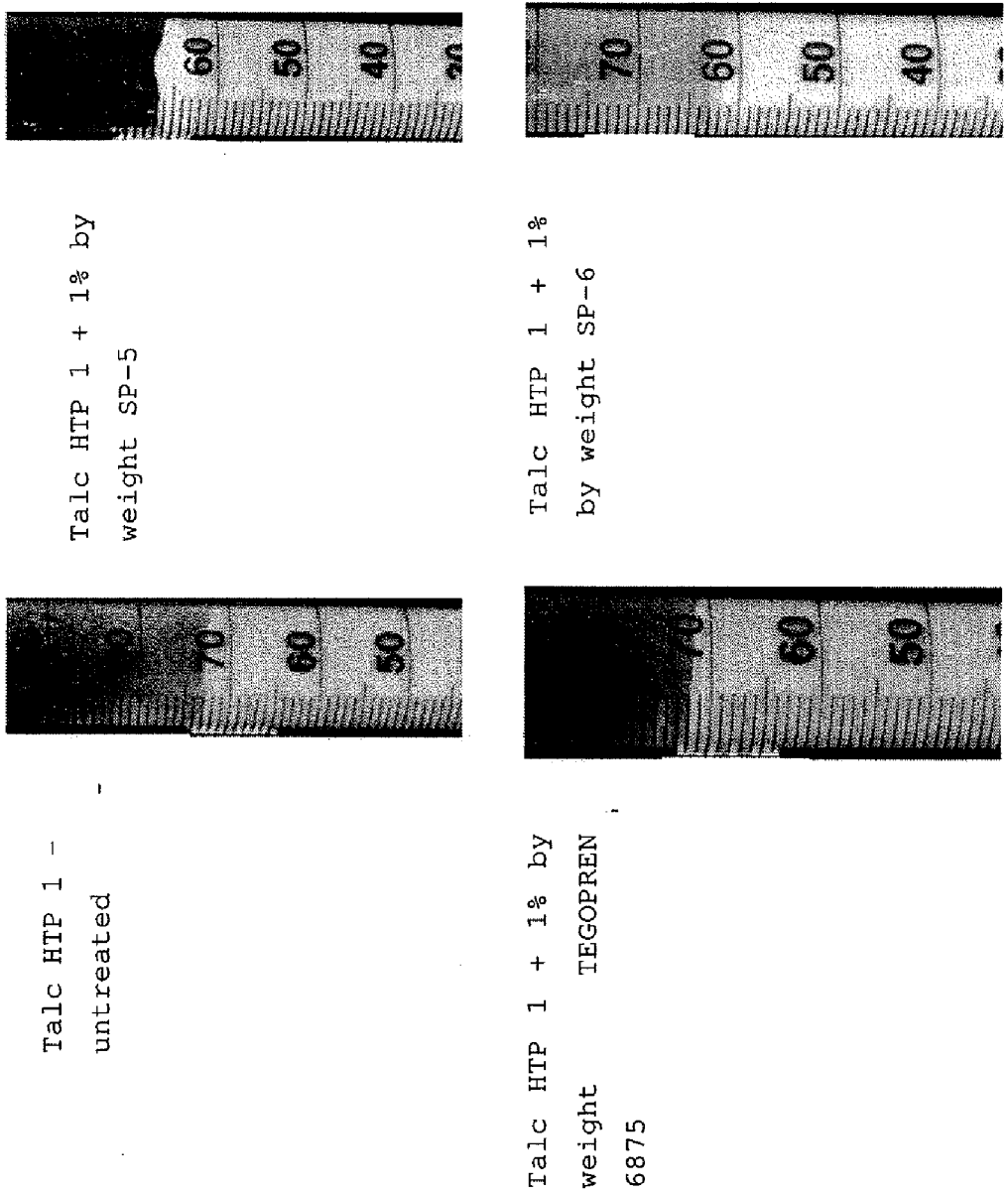
FIG. 5 shows a number of results for the determination of the bulk densities from Example 9, in order to illustrate the reduced bulk densities.

For illustration of the reduced bulk densities, see also FIG. 3.

Example 10

Inventive Dispersion of Fillers in a Polymer Compound Based on Polypropylene, Corresponding to Separate Addition of the Silyl Compounds Using a Leistritz extruder 27 mm (twin-screw extruder from Leistritz), at 200 rpm, the following filler compound formulas were produced:

| Polypropylene PPH 9069 | 39.8% |
|---|---|
| Irganox 1010 | 0.2% |
| Luzenac 20 MO or Millicarb OG | 60.0% |

These are compared here with the formulas comprising the polyethers of formula 1:

| Polypropylene PPH 9069 | 37.8% |
|---|---|
| Irganox 1010 | 0.2% |
| Additive (non-inventive or inventive) | 2.0% |
| Luzenac 20 MO or Millicarb OG | 60.0% |

Noninventive products used for the dispersing of fillers and pigments are typically employed stearates, waxes or else high-value copolymers (TEGOMER P 121 and E 525). The compounds must be tested for their mechanical properties in order to be able to assess the binding of the filler to the polymer matrix and in order to be able to classify the degree of dispersion, which is improved by the hydrophobization of the filler surfaces. For these purposes the following properties were tested:

1. Impact strength (IS) and notched impact strength (NIS) in kJ/m2 in accordance with Izod ISO Standard
2. Elongation (Eta) in percent in accordance with DIN 53455

Furthermore, the MFI (Melt Flow Index) of the compounds was determined in accordance with DIN ISO 53735, for which, in the case of polypropylene compounds, the amount in grams of compound per 10 minutes of flow was determined and the temperature amounts to 230° C. with an applied weight of 2.16 kilograms.

The values determined are given in Table 4 below:

TABLE 4

| Compound | IS kJ/m2 | NIS kJ/m2 | Eta % | MFI (230° C./2.16 kg) g/10 min |
|---|---|---|---|---|
| Millicarb OG (calcium carbonate) | | | | |
| No additive | 11.18 | 1.44 | 0.7 | 13 |
| TEGOMER P 121 | 11.85 | 1.74 | 0.9 | 15 |
| SP-5 | 32.15 | 2.09 | 2.4 | 18 |
| SP-7 | 23.88 | 2.08 | 0.9 | 15 |
| SP-6 | 13.49 | 2.06 | 1.0 | 16 |
| Luzenac 20 MO (talc) | | | | |
| No additive | 5.42 | 1.21 | — | 8 |
| TEGOMER E 525 | 5.67 | 1.22 | — | 6 |
| TEGOMER P 121 | 5.87 | 1.22 | — | 10 |
| SP-5 | 6.09 | 1.34 | — | 14 |
| SP-6 | 6.05 | 1.35 | — | 15 |
| SP-7 | 6.46 | 1.33 | — | 14 |

From a closer viewing of the results in the compounds it becomes apparent that the inventive products, relative to the noninventive products which presently correspond to the highest state of the art, exhibit a markedly better binding of the fillers to the polymer matrix, because the inventive products display a distinct improvement in impact strength and notched impact strength, without at the same time producing any loss in the flexibility of the compound—as indicated by the elongation in per cent. The inventive products permit a much higher economy, since the MFI is always higher than without additive or with non-inventive products. For extrusion operations, therefore, a throughput of up to twice the level can be expected, and a significant improvement in energy efficiency is recorded.

Example 11

Inventive Surface Modification of Talc Particles with Silyl Polyethers 1 and Detection of Attachment by Thermogravimetric Analysis of the Particles (Loss of Ethanol on Attachment)

a) Modification of IMIFABI HTP 1 Talc with 1% by Weight Polyether SP-8

A Henschel mixer was charged with 198 g of IMIFABI HPT 1 talc. With vigorous mixing (1000 rpm), 2 g of polyether SP-8 were injected slowly through a septum. Mixing was continued for 20 minutes more following the addition of the silyl polyether. In the course of this mixing, the temperature rose up to 75° C. Thermogravimetric analysis (RT to 800° C., 5° C./min, air) indicated a mass decrease of 0.76% by weight in the temperature range from 140 to 330° C. (calculated value for the mass decrease due to oxidation: ~0.89% by weight).

b) Modification of IMIFABI HTP 1 Talc with 1% by Weight Polyether SP-1

A Henschel mixer was charged with 198 g of IMIFABI HPT 1 talc. With vigorous mixing (1000 rpm), 2 g of polyether SP-1 were injected slowly through a septum. Mixing was continued for 20 minutes more following the addition of the silyl polyether. In the course of this mixing, the temperature rose up to 75° C. Thermogravimetric analysis (RT to 800° C., 5° C./min, air) indicated a mass decrease of 0.64% by weight in the temperature range from 140 to 330° C. (calculated value for the mass decrease due to oxidation: ~0.74% by weight).

In both cases the mass decrease observed was well below the figure for the inventive silyl polyether used for surface modification (1% by weight), which suggests the elimination of ethanol and the covalent attachment of the silyl polyether to the substrate.

Example 12

Inventive Surface Modification of Planar $SiO_2$ Surfaces with Silyl Polyethers 1 and Determination of the Temperature-dependent Contact Angle with Respect to Water The substrates employed were pretreated Si wafers which had an oxidic surface. This surface ought to exhibit reactive hydroxyl groups in order to allow the attachment of an inventive silyl polyether. For this purpose, two different pre-treatment techniques were employed: a) The wafer sections were calcined at 1000° C. in air for one hour and stored overnight in dilute (5% strength) aqueous ammonia solution. Thereafter the specimens were rinsed with demineralized water and stored in demineralized water up to the time of their further use. b) The wafer sections were immersed for one minute into a freshly prepared mixture of concentrated $H_2SO_4$ and 30% strength $H_2O_2$ in a ratio of 1:1, then rinsed with demineralized water and stored in demineralized water up until the time of their further use.

It is known that randomly distributed EO/PO polyethers possess a cloud point—that is, they are soluble to give a clear solution in water only up to a certain temperature, above which these solutions become cloudy as a result of precipitation of the polyether. Polyether structures of this kind with an EO/PO distribution of 25/75 are represented by polyethers SP-9 and SP-10. Both polyethers were coupled to the pretreated wafer surfaces via a hydrolysis-condensation reaction.

1% strength by weight solutions of both silyl polyethers in anhydrous ethanol were prepared, and the pretreated wafers were rinsed with ethanol and placed in the ethanolic silyl polyether solution. After overnight standing, the treatment solutions were acidified to a pH of 1-2 using concentrated HCl, and after a further three hours the solutions were admixed with demineralized water as well, making the water content of the treatment solutions approximately 1% by weight. Following further overnight standing, the coated wafers were washed with water and then with ethanol and were dried at room temperature in air.

The dynamic contact angle with respect to water of the substrates thus coated was determined at a number of locations thereon, at 20 and at 50° C. On the basis of the behaviour of a corresponding polyether in water at these temperatures it was expected that the higher temperature ought to result in a more hydrophobic surface of the coated wafers. The results are shown in Table 5 below:

TABLE 5

| Coated substrate | Averaged contact angle at 20° C. | Averaged contact angle at 50° C. |
|---|---|---|
| Blank value (etched Si wafer, uncoated) | 52° | 44° |
| Etched Si wafer, coated with SP-9 | 50° | 57° |
| Etched Si wafer, coated with SP-10 | 46° | 54° |
| Calcined Si wafer, coated with SP-9 | 43° | 48° |

Having thus described in detail various embodiments of the present invention, it is to be understood that the invention defined by the above paragraphs is not to be limited to particular details set forth in the above description as many apparent variations thereof are possible without departing from the spirit or scope of the present invention.

The invention claimed is:

1. A method of modifying and/or coating a surface which comprises:

applying one or more mixed curable hydroxyl-containing silyl polyethers having at least one non-terminal sily function to the surface;

wherein the one or more mixed curable hydroxyl-containing silyl polyethers is a compound of formula (1);

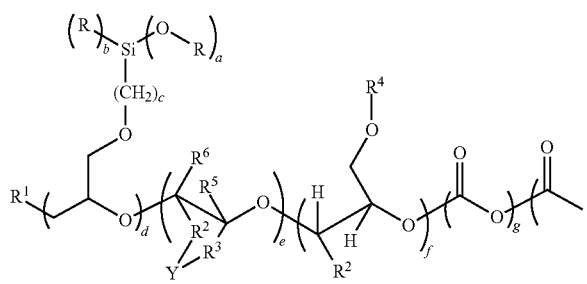

-continued

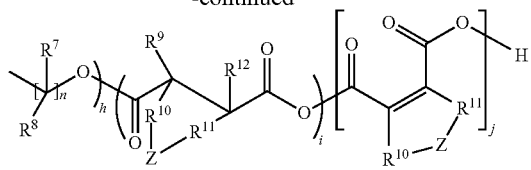

where a is an integer from 1 to 3;
where b is an integer from 0 to 2;
where the sum of a and b is 3;
where c is an integer from 0 to 22;
where d is an integer from greater than 1 to 1000;
where e is an integer from 0 to 10 000;
where f is an integer from 0 to 1000;
where is an integer from 0 to 1000;
where h, i and j are integers from 0 to 500;
  with the proviso that the fragments having the indices d to j are freely permutable with one another, i.e. are interchangeable in the sequence within the polyether chain;

where n is an integer between 2 and 8;

where R represents one or more identical or different radicals selected from linear or branched, saturated, singularly or multiply unsaturated alkyl radicals having 1 to 20 carbon atoms or haloalkyl groups having 1 to 20 carbon atoms;

where $R^1$ is a saturated or unsaturated, optionally branched radical which is attached via an oxygen atom, or is a polyether radical of the type of an alkoxy, arylalkoxy or alkylarylalkoxy group, in which the carbon chain may be interrupted by oxygen atoms, or is an optionally singularly or multiply fused aromatic aryloxy group, or is a silicon compound or a siloxane radical, which may be substituted by alkyl and/or aryl groups;

where $R^2$ or $R^3$, and $R^5$ or $R^6$, is or else are independently of one another H or a saturated or optionally singularly or multiply unsaturated, including further substituted, optionally monovalent or polyvalent hydrocarbon radical, the radicals $R^5$ or $R^6$ being a monovalent hydrocarbon radical, it being possible for the hydrocarbon radical to be bridged cycloaliphatically via the fragment Y; Y may be absent, or else may be a methylene bridge having 1 or 2 methylene units; if Y is absent, then or $R^2$ $R^3$ independently of one another are each a linear or branched radical having 1 to 20 carbon atoms;

where $R^4$ is a linear or branched alkyl radical of 1 to 24 carbon atoms or an aromatic or cycloaliphatic radical, winch optionally may in turn carry alkyl groups;

where $R^7$ and $R^8$ are independently of one another either hydrogen, or alkyl, al-koxy, aryl or aralkyl groups which arc copolymerized by ring-opening polymerization to give crosslinkable polyether esters containing alkoxysilane groups; and where $R^9$, $R^{10}$, $R^{11}$ and $R^{12}$ are independently of one another either hydrogen or alkyl, alkenyl, alkoxy, aryl or aralkyl groups, it being possible for the hydrocarbon radical to he bridged cycloaliphatically or aromatically via the fragment Z, and it being possible for Z to be a divalent alkylene or alkenylene radical.

2. The method of claim 1 wherein compounds of the formula (1) used are compounds of the formula (5), or mixtures thereof, the formula (5) being:

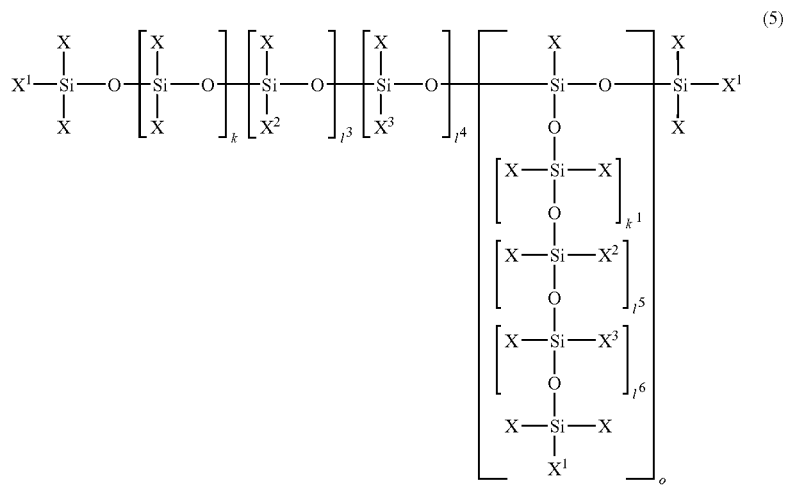

where X is a linear, cyclic or branched, aliphatic or aromatic, saturated or unsaturated hydrocarbon radical having 1 to 20 C atoms, which may contain oxygen, nitrogen, phosphorus, or sulphur;

where $X^1$ is optionally X, $X^2$ or $X^3$;

where $X^2$ is an alkoxysilyl-bearing, OH-functional polyoxyalkylene radical of the formula (5a) which may be ester- or carbonate-modified;

aryl or aralkyl groups, the hydrocarbon radical being bridged cycloaliphatically or aromatically via the fragment Z, it being possible for Z to be a divalent alkylene or else alkenylene radical; and wherein $R^{13}$ is optionally an alkyl group having 1 to 18 C atoms, or a polyoxyalkylene radical which is terminally esterified with a monofunctional carboxylic acid, of the formula (5c);

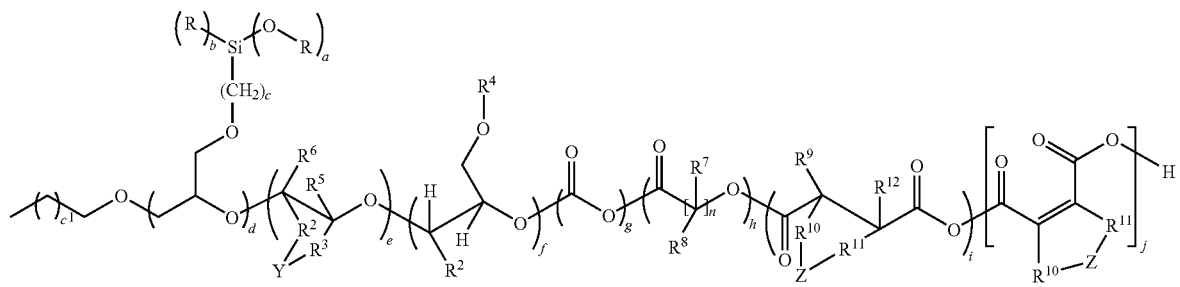
(5a)

where $X^3$ is a terminally etherified polyoxyalkylene radical of the formula (5b);

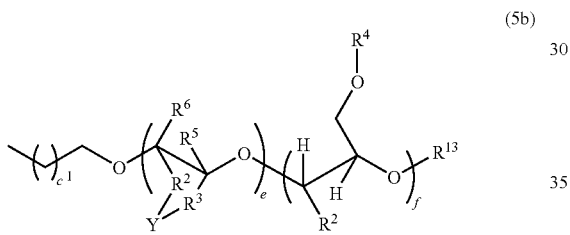
(5b)

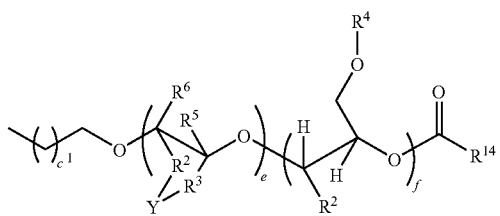
(5c)

where $R^{14}$ is a saturated or a singularly or multiply unsaturated, either linear or branched, aliphatic or aromatic hydrocarbon radical having 1-30 carbon atoms, which in its turn may carry OH groups;

where $X^4$ is either $X^1$ or the fragment of the formula (5d);

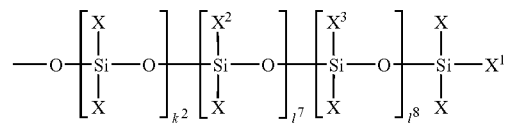
(5d)

where R represents one or more identical or different radicals selected from linear or branched, saturated, singularly or multiply unsaturated alkyl radicals having 1 to 20 carbon atoms or haloalkyl groups having 1 to 20 carbon atoms;

where $R^2$ or $R^3$, and $R^5$ or $R^6$, are each or independently of one another H or a saturated or optionally singularly or multiply unsaturated, including further substituted, optionally monovalent or polyvalent hydrocarbon radical, the radicals $R^5$ or $R^6$ being a monovalent hydrocarbon radical, and it being possible for the hydrocarbon radical to be bridged cycloaliphatically by the fragment Y; Y may be absent, or else may be a methylene bridge having 1 or 2 methylene units; if Y is absent, then $R^2$ or $R^3$ independently of one another are each a linear or branched radical having 1 to 20 carbon atoms, and the hydrocarbon radicals $R^2$ and $R^3$ may in turn be further substituted and carry functional groups such as halogens, hydroxyl groups or glycidyloxypropyl groups;

where $R^4$ is a linear or branched alkyl radical of 1 to 18 carbon atoms, which may be attached to an aromatic or cycloaliphatic radical;

where $R^7$ and $R^8$ are independently of one another either hydrogen or alkyl alkoxy, aryl, or aralkyl groups;

where $R^9$, $R^{10}$, $R^{11}$ and $R^{12}$ are independently of one another either hydrogen or alkyl, alkenyl, alkoxy, where k, $k^1$ and $k^2$ independently of one another are integers from 0 to 500;

where $l^3$, $l^4$, $l^5$, $l^6$, $l^7$ and $l^8$ independently of one another are integers from 0 to 60; and where o is an integer from 0 to 10;

with the proviso that;

X is at least once $X^2$, if the sum of $l^3$, $l^5$ and $l^7$ is zero; and the sum of $l^3$, $l^5$ and $l^7$ is at least 1 if $X^1$ is other than $X^2$;

where a is an integer from 1 to 3;
where b is an integer from 0 to 2;
where the sum of a and b is 3;
where c is an integer from 0 to 22;

where $c^1$ is an integer from 0 to 24;
where d is an integer from 1 to 500;
where e is an integer from 0 to 5000;
where n is an integer from 2 to 8; and
where f, g, h, i and j are each integers from 0 to 500;
with the proviso that the fragments having indices d to j are freely permutable with one another, interchangeable in the sequence within the polyether chain, it being possible for the various monomer units of the fragments having the index numbers d to j to be of blockwise structure with one another or else to be subject to a statistical distribution; and
with the proviso that the fragments having the indices k, $k^1$, $k^2$, $l^3$, $l^4$, $l^5$, $l^6$, $l^7$, $l^8$, and o are freely permutable with one another, interchangeable within the siloxane chain, and may optionally be present in random distribution or in blocklike array.

3. The method of claim 1;
wherein linear polyether-siloxane-polyether triblock copolymers of the formula (6) are present in which the polyether chains furnished with alkoxysilyl groups are bonded via an Si—O—C linkage, b, to the siloxane structure, the formula (6) being;

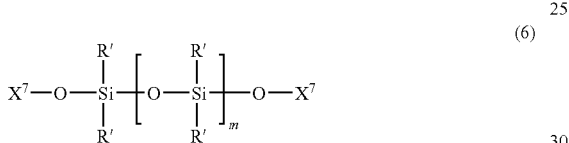

(6)

where $R^1$ corresponds to one or more identical or different linear or branched, saturated, singularly or multiply unsaturated alkyl radicals having 1 to 20 carbon atoms;
where m is an integer from 0 to 5000; and
where $X^7$ corresponds to the polyether fragment of the formula (6a);

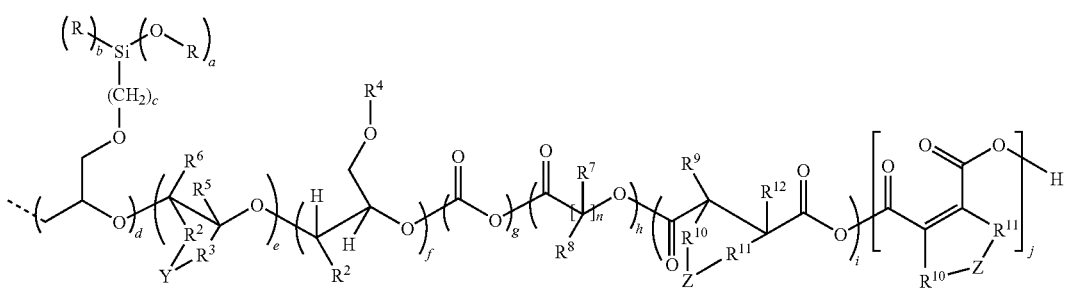

(6a)

where the substituents R, $R^2$—$R^{12}$, the radicals Y and Z and the indices a, b, c, d, e, f, g, h, i, j, and n correspond to the definitions specified above for the compounds of the Formula (5a).

4. The method of claim 3;
wherein, in addition to the silyl polyether, further monomeric silanes or α,ω-silyl-terminated prepolymers are used.

5. A composition for surface modification or coating, comprising
at least one compound of:
the formula (1) as described in claim 1;
the formula (5) as described in claim 2 and/or
the formula (6) as described in claim 3.

6. A composition comprising:
the silyl polyethers of formula (1) as described in claim 1; and
other silyl compounds.

7. The composition of claim 6;
wherein the other silyl compounds is a compound of the formula (2);

$A_xSiB_{(4-x)}$ (2);

where A represents identical or different nonhydrolysable groups, B=identical or different hydrolysable groups or hydroxyl groups, and x=1, 2, 3 or 4, and/or, as further components, monomeric, oligomeric or polymeric silanes or components bearing reactive silyl groups, as selected from the group encompassing acrylates, epoxides, isocyanates, carboxylates, hydroxides, lactones, lactams.

8. Composition according to claim 7;
where, for the silyl polyether 1 of the formula (1), it is the case that d>1.

9. A method for surface modifying particles or planar structures, the method comprising:
applying compositions comprising prepolymers of the formula (1) as described in claim 1, with mixing and/or in the presence of crosslinking catalysts, in pure form or comprising organic and/or inorganic solvents, to the particle surfaces or from emulsions, where they then are able to react to completion with covalent or physical attachment.

10. The method for surface modifying particle surfaces of claim 9;
wherein the particles, or the particles dispersed in a matrix, are modified by addition of the silyl polyethers with thorough mixing and, optionally, addition of a suitable catalyst.

11. The method of claim 10;
whereein surfaces for modification that are used are inorganic and/or organic particles and/or organomodified particles and/or mixtures thereof with one another.

* * * * *